(12) United States Patent
Mather et al.

(10) Patent No.: US 9,982,163 B2
(45) Date of Patent: May 29, 2018

(54) WATERBORNE SHAPE MEMORY POLYMER COATINGS

(71) Applicant: Syracuse University, Syracuse, NY (US)

(72) Inventors: Patrick Mather, Syracuse, NY (US); Kazuki Ishida, Syracuse, NY (US); Pamela Wilson, South Euclid, OH (US)

(73) Assignee: Syracuse University, Syracuse, NY (US)

(*) Notice: Subject to any disclaimer, the term of this patent is extended or adjusted under 35 U.S.C. 154(b) by 708 days.

(21) Appl. No.: 13/645,593

(22) Filed: Oct. 5, 2012

(65) Prior Publication Data
US 2014/0099848 A1   Apr. 10, 2014

(51) Int. Cl.
| | |
|---|---|
| *C09D 175/04* | (2006.01) |
| *A61K 8/87* | (2006.01) |
| *D02G 3/36* | (2006.01) |
| *C08G 18/66* | (2006.01) |
| *C08G 18/67* | (2006.01) |
| *C08G 18/10* | (2006.01) |
| *C09D 175/12* | (2006.01) |
| *C08G 18/42* | (2006.01) |
| *D06M 15/00* | (2006.01) |
| *D06M 15/507* | (2006.01) |
| *D06M 15/568* | (2006.01) |
| *D06M 15/572* | (2006.01) |

(Continued)

(52) U.S. Cl.
CPC ............ *C09D 175/04* (2013.01); *A61K 8/87* (2013.01); *A61Q 5/04* (2013.01); *A61Q 5/06* (2013.01); *C08G 18/10* (2013.01); *C08G 18/4277* (2013.01); *C08G 18/6655* (2013.01); *C08G 18/675* (2013.01); *C09D 175/12* (2013.01); *D02G 3/36* (2013.01); *D06M 15/00* (2013.01); *D06M 15/507* (2013.01); *D06M 15/568* (2013.01); *D06M 15/572* (2013.01); *C08G 2280/00* (2013.01); *Y10T 428/2933* (2015.01); *Y10T 442/20* (2015.04)

(58) Field of Classification Search
CPC ... C08G 18/4277; C08G 2280/00; A61K 8/87
USPC ........................................... 442/59; 428/375
See application file for complete search history.

(56) References Cited

U.S. PATENT DOCUMENTS

| 7,067,606 B2 | 6/2006 | Mather et al. |
| 7,091,297 B2 | 8/2006 | Mather et al. |

(Continued)

FOREIGN PATENT DOCUMENTS

| CN | 1704523 | 12/2005 |
| WO | 2005046470 | 5/2005 |

(Continued)

OTHER PUBLICATIONS shape memory properties of semented polymers containing aramid hard segments and PCL soft segments, Schuh et al., polymers, 2010, pp. 71-85.*

(Continued)

*Primary Examiner* — Vincent A Tatesure
(74) *Attorney, Agent, or Firm* — Bond, Schoeneck & King, PLLC; Frederick Price

(57) ABSTRACT

The present invention relates to shape memory polymers and waterborne coating materials and, more particularly, to waterborne shape memory polymer coatings.

5 Claims, 27 Drawing Sheets

(51) Int. Cl.
A61Q 5/04 (2006.01)
A61Q 5/06 (2006.01)

(56) References Cited

U.S. PATENT DOCUMENTS

| | | | |
|---|---|---|---|
| 7,151,157 | B2 | 12/2006 | Mather |
| 7,173,096 | B2 | 2/2007 | Mather |
| 2004/0116641 | A1 | 6/2004 | Mather et al. |
| 2005/0244353 | A1 | 11/2005 | Lendlein |
| 2008/0085946 | A1* | 4/2008 | Mather et al. ............... 522/4 |
| 2010/0256777 | A1* | 10/2010 | Datta et al. ............ 623/23.72 |
| 2011/0282022 | A1* | 11/2011 | Tong ......................... 526/279 |

FOREIGN PATENT DOCUMENTS

| WO | WO2008130650 | 10/2008 |
|---|---|---|
| WO | WO2011115582 | 9/2011 |

OTHER PUBLICATIONS

Behl, M., Razzaq, M.Y., Lendlein, A., Multifunctional Shape-Memory Polymers, Advanced Materials, 2010, pp. 3388-3410, vol. 22, Wiley-VCH.

Yakacki, C., Gall, K., Shape-Memory Polymers for Biomedical Applications, Advanced Polymer Science, 2009, Springer-Verlag Berlin Heidelberg.

Hu, J., Chen, S., A Review of Actively Moving Polymers in Textile Applications, Journal of Materials Chemistry, 2010, pp. 3346-3355, vol. 20, The Royal Society of Chemistry.

Jung, Y.C., So, H.H., Cho, J.W., Water-Responsive Shape Memory Polyurethane Block Copolymer Modified with Polyhedral Oligomeric Silsesquioxane, Journal of Macromolecular Science, 2006, pp. 453-461, vol. 45, Taylor and Francis Group, LLC.

Li, J., Yan, W., Jing, L., Xeuyong, L., Yuejun, L., Wangzhou, L., Shaozong, C., Addition of al Alginate to a Modified Zeolite Improves Hemostatic Performance in a Swine Model of Lethal Groin Injury, The Journal of Trauma Injury, Infection, and Critical Care, 2009, pp. 612-620.

Neuhoff, P., Wang, J., Heat Capacity of Hydration in Zeolites, American Mineralogist, 2007, pp. 1358-1367, vol. 92.

Neuhoff, P., Wang, J., Isothermal Measurement of Heats and Hydration in Zeolites by Simultaneous Thermogravimetry and Differential Scanning Calorimetry, Clays and Clay Materials, 2007, pp. 239-252, vol. 55, The Clay Minerals Society.

Carey, J.W., Bish, D., Calorimetric Measurement of the Enthalpy of Hydration of Clinoptilolite, Clay and Clay Materials, 1997, pp. 826-833, vol. 45, The Clay Minerals Society.

Suzuki, M., Ohashi, F., Inukai, K., Maeda, M., Tomura, S., Misota, T., Hydration Enthalpy Measurement and Evaluation as Heat Exchangers of Allophane and Imogolite, Journal of Ceramic Society of Japan, 2001, pp. 681-685, vol. 109.

Lendlein, A., Kelch, S., Shape-Memory Polymers, Angew. Chem. Int. Ed 2002, pp. 2034-2057, vol. 41, Wiley-VCH, Weinheim, Germany.

Ishida, K., Yoshie, N., Two-Way Conversion Between Hard and Soft Properties of Semicrystalline Cross-Linked Polymer, Macromolecules, 2008, pp. 4753-4757, vol. 41, American Chemical Society.

Luo, H., Liu, Y., Yu, Z., Zhang, S., Li, B., Novel Biodegradable Shape Memory Material Based on Partial Inclusion Complex Formation Between Cyclodextrin and Poly Captolactone, Biomacromolecules, 2008, pp. 2573-2577, vol. 9, American Chemical Society.

Gonzalez-Garcia, Y., Mol, J.M.C., Muselle, T., Degraeve I., Van Assche, G., Scheltjens, G., Van Mele, B., Terryn, H., A Combined Mechanical, Microscopic and Local Electrochemical Evaluation of Self-Healing Properties of Shape-Memory Polyurethane Coatings, Electrochimica Acta, 2011, pp. 9619-9626, vol. 56, Elsevier, Ltd.

Kim, B.K., Lee, S.Y., Xu, M., Polyurethanes Having Shape Memory Effects, Polymer, 1996, pp. 5781-5793, vol. 37, Elsevier.

Lendlien, A., Langer, R., Biodegradable, Elastic Shape-Memory Polymers for Potential Biomedical Applications, Science, 2002, pp. 1673-1676, vol. 296.

Ping, P., Wang, W., Chen, X., Jing, X., Poly Caprolactone Polyurethane and its Shape-Memory Property, Biomacromolecules, 2005, pp. 587-592, vol. 6, American Chemical Society.

Knight, P., Lee, K.M., Qin, H., Mather, P., Biodegradable Thermoplastic Polyurethanes Incorporating Polyhedral Oligosilsesquioxane, Biomacromolecules, 2005, pp. 2458-2467, vol. 9m American Chemical Society.

Nanda, A., Wicks, D., The Influence of the Ionic Concentration, Concentration of the Polymer, Degree of Neutralization and Chain Extension on Aqueous Polyurethane Dispersions Prepared by the Acetone Process, Polymer, 2006, pp. 1805-1811, vol. 47, Elsevier.

Yen, M.S., Tsai, P.Y., Hong, P.D., The Solution Properties and Membrane Properties of Polydimethylsiloxane Waterborne Polyurethane Blended with the Waterborne Polyurethanes of Various Kinds of Soft Segments, Colloids and Surfaces, 2006, pp. 1-9, vol. 279, Elsevier.

Jeong, H.Y., Lee, M.H., Kim, B.K., Surface Modification of Waterborne Polyurethane, Colloids and Surfaces, 2006, pp. 178-185, vol. 290, Elsevier.

Kim, Y.B., Chung, C.W., Kim, H.W., Rhee, Y.H., Shape Memory Effect of Bacterial Poly(3-Hydroxybutyrate)-co-(3-hyrdoxyvalerate), Macromolecular Rapid Communications, 2005, pp. 1070-1074, vol. 26, Wiley-VCH.

Xu, J., Song, J., High Performance Shape Memory Polymer Networks Based on Rigid Nanoparticle Cores, PNAS, 2010, pp. 7652-7657, vol. 107.

Serrano, M.C., Carbajal, L., Ameer, G., Novel Biodegradable Shape-Memory Elastomers with Drug-Releasing Capabilities, Advanced Materials, 2011, pp. 2211-2215, vol. 23, Wiley-HCH.

Cho, J., Hung, Y., Chun, B., Chung, Y., Water Vapor Permeability and Mechanical Properties of Fabrics Coated with Shape-Memory Polyurethane, Journal of Applied Polymer Science, 2004, pp. 2812-2816, vol. 92, Wiley Periodicals, Inc.

Mondal, S., Hu, J., Water Vapor Permeability of Cotton Fabrics Coated with Shape Memory Polyurethane, Carbohydrate Polymers, 2007, pp. 282-287, vol. 67, Elsevier.

Ali A. Srinivasan, K., Synthesis, Characterization, and Studies on the Solid-State Crosslinking of Functionalized Vinyl Cinnamate Polymers, Journal of Applied Polymer Science, 1998, pp. 441-448, vol. 67, John Wiley & Sons, Inc.

Lendlein, A., Jiang, H., Junger, O., Langer, R., Light-Induced Shape-Memory Polymers, Letters to Nature, 2005, pp. 879-882, vol. 434, Nature Publishing Group.

Kaneko, T., Thi, T., Shi, D., Akashi, M., Environmentally Degradable, High-Performance Thermoplastics from Phenolic Phytomonomers, Letters to Nature, 2006, pp. 966-970, vol. 5, Nature Publishing Group.

Nagata, M., Inaki, K., Synthesis and Characterization of Photocrosslinkable Poly Lactides with a Pendant Cinnamate Group, Eauropean Polymer Journal, 2009, pp. 1111-1117, vol. 45, Elsevier.

Garle, A., Kong, S., Ojha, U., Budhlall, B., Thermoresponsive Semicrystalline Poly Caprolactone Networks: Exploiting Cross-Linking with Cinnamoyl Moieties to Design Polymers with Tunable Shape Memory, Applied Materials and Interfaces, 2012, pp. 645-657, vol. 4, American Chemical Society.

Gupta, P., Trenor, S., Long, T., Wilkes, G., In Situ Photo-Cross-Linking of Cinnamate Functionalized Polymethyl Methacrylate-co-2-Hydrocyethyl Acrylate Fibers During Electrospinning, Macromolecules, 2004, pp. 9211-9218, vol. 37, American Chemical Society.

Andreopoulos, F., Beckman, E., Russell, A., Photoswitchable PEG-CA Hydrogels and Factors that Affect their Photosensitivity, Journal of Polymer Science, 2000, pp. 1466-1476, vol. 38, John Wiley & Sons, Inc.

Zheng, Y., Andreopoulos, F., Micic, M, Huo, Q., Pham, S., Leblanc, R., A Novel Photoscissile Polyethylene Glycol Based Hydrogel, Advanced Functional Materials, 2001, pp. 37-40, vol. 11, Wiley-VCH.

(56) References Cited

OTHER PUBLICATIONS

Shi, D., Matsusaki, M., Kaneko, T., Akashi, M., Photo-Cross-Linking and Cleavage Induced Reversible Size Change of Bio-Based Nanoparticles, Macromolecules, 2008, pp. 8167-8172, vol. 41, American Chemical Society.

Hu, X., Chen, X., Cheng, H., Jing, X., Cinnamate-Functionalized Poly(ester-carbonate): Synthesis and its UV Irradiation-Induced Photo-Crosslinking, Journal of Polymer Science, 2009, pp. 161-169, vol. 47, Wiley Periodicals, Inc.

Chen, S., Chan, W., Polyurethane Cationomers. I. Structure-Property Relationships, Journal of Polymer Science, 1990, pp. 1499-1514, vol. 28, John Wiley & Sons, Inc.

Orler, E., Moore, R., Influence of Ionic Interactions on the Crystallization of Lightly Sulfonated Syndiotactic Polystyrene Ionomers, Macromolecules, 1994, pp. 4774-4780, vol. 27, American Chemical Society.

Orler, E., Calhoun, B., Moore, R., Crystallization Kinetis as a Probe of the Dynamic Network in Lightly Sulfonated Syndiotactic Polystyrene Ionomers, Macromolecules, 1996, pp. 5965-5971, vol. 29, American Chemical Society.

Quiram, D., Register, R., Crystallization and Ionic Associations in Semicrystalline Ionomers, Macromolecules, 1998, pp. 1432-1435, vol. 31, American Chemical Society.

Han, S., Im, S., Kim, D., Dynamic Mechanical and Melt Rheological Properties of Sulfonated Poly(butylene Succinate) Ionomers, Polymer, 2003, pp. 7165-7173, vol. 44, Elsevier.

Ishida, K., Han, S., Inoue, Y., Im, S., Novel Poly(butylene Succinate)-Based Ionomers with Sulfonated Succinate Units: Synthesis, Morphology, and the Unique Nucleation Effect on Crystallization, Macromolecular Chemistry and Physics, 2005, pp. 1028-1034; vol. 206, Wiley-VCH.

Ishida, K., Han, S., Im, S., Inoue, Y., Effects of Fusion Temperature and Metal Ion Variation on Crystallization of Lightly Ionized Poly(butylene Succinate), Macromolecular Chemistry and Physics, 2007, pp. 146-154, vol. 208, Wiley-VCH.

Lim, J., Lee, Y., Im, S., Influence of Ionic Association on the Nonisothermal Cyrstallization Kinetics of Sodium Sulfonate Poly(butylene succinate) Ionomers, Journal of Polymer Science, 2008, pp. 925-937, vol. 46, Wiley Periodicals, Inc.

Jones, L., Rivett, D., The Role of 18-Methyleicosanoic Acid in the Structure and Formation of Mammalian Hair Fibres, Mircom, 1997, pp. 469-485, vol. 28, Pergamon.

Swift, J., Smith, J., Microscopical Investigations on the Epicuticle of Mammalian Keratin Fibres, Journal of Microscopy, 2001, pp. 203-211, vol. 204, The Royal Microscopical Society.

Gamez, Garcia, M., Plastic Tielding and Fracture of Human Hair Cuticles by Cyclical Torsion Stresses, J. Cosmet. Sci., 1999, pp. 69-77, vol. 50.

Voit, W., Ware, T., Dasari, R., Smith, P., Danz, L., Simon, D., Barlow, S., Marder, S., Gall, K., High-Strain Shape-Memory Polymers, Advanced Functional Materials, 2010, pp. 162-171, vol. 20, Wiley VCH.

Ni, Y., Zheng, S., A Novel Photocrosslinkable Polyhedral Oligomeric Silsesquioxane and its Nanocomposites with Poly(vinyl Cinnamate)., Chem. Mater., 2004, pp. 5141-5148, vol. 16, American Chemical Society.

Chung, C.M., Roh, Y.S., Cho, S.Y., Kim, J.G., Crack Healing in Polymeric Materials via Photochemical (2+2) Cycloaddition, Chem Mater, 2004, pp. 3982-3984, vol. 16, American Chemical Society.

Madbouly, S., Otaigbe, J., Recent Advances in Synthesis, Characterization and Theological Properties of Polyurethanes and Poss/Polyurethane Nanocomposites Dispersions and Films, Progress in Polymer Science, 2009, pp. 1283-1332, vol. 34, Elsevier.

Chan, W., Chen, S., Polyurethane Ionomers: Effects of Emulsification on Properties of Hexamethylene Diisocyanate-Based Polyether Polyurethane Cationomers, Polymer, 1988, pp. 1995-2001, vol. 29, Butterworth & Co, Ltd.

Tsai, H., Hong, P., Yen, M., Preparation and Physical Properties of Mdea-based Polyurethane Cationomers and their Application to Textile Coatings, Textile Research Journal, 2007, pp. 710-720, vol. 77, SAGE Publications.

Yang, B., Huang, W., Li, C., Li, L., Effects of Moisture on the Thermomechanical Properties of the Polyurethane Shape Memory Polymer, Polymer, 2006, pp. 1348-1359, vol. 47, Elsevier.

Lv, H., Leng, J., Liu, Y., Du, S., Shape-Memory Polymer in Response to Solution, Advanced Engineering Materials, 2008, pp. 592-595, vol. 10, Wiley-VCH.

Chen, M., Tsai, H., Chang, Y., Lai, W., Mi, F., Liu, C., Wong, H., Sung, H., Rapidly Self-Expandable Polymeric Stents with a Shape-Memory Property, Biomacromolecules, 2007, pp. 2447-2780, vol. 8, American Chemical Society.

Ostomel, T., Stoimenov, P., Holden, P., Alam, H., Stucky, G., Host-Guest Composites for Induced.Hemostasis and Therapeutic Healing in Traumatic Injuries, J. Thromb Thrombolysis, 2006, pp. 55-67, vol. 22, Springer Science + Business Media, LLC.

Liu, C., Qin, H., Mather, T., Review of Progress in Shape-Memory Polymers, J. Mater. Chem, 2007, pp. 1543-1558, vol. 17, The Royal Society of Chemistry.

Mather, P., Luo, X., Rousseau, I., Shape Memory Polymer Research, The Annual Review of Materials, 2009, pp. 445-471, vol. 39.

Kunzelman, J., Chung, T., Mather, P., Weder, C., Shape Memory Polymers with Built-In Threshold Temperature Sensors, Journal of Materials Chemistry, 2008, pp. 1082-1086, vol. 18, The Royal Society of Chemistry.

Lee, K.M. et al., "Polycaprolactone-POSS Chemical/Physical Double Networks", Macromolecules, Jun. 13, 2008, vol. 41, pp. 4730-4738, see pp. 4730-4732.

Internationl Search Report Form PCT/ISA/220, International Application No. PCT/US2013/063709, pp. 1-11, dated Nov. 27, 2013.

PCT International Search Report dated Apr. 16, 2015.

\* cited by examiner

Synthesis of 2-ethyl-2-cinnamoyloxymethyl-1,3-propanediol (ECMPD).

(a)

(b)

WATERBORNE SHAPE MEMORY POLYMER COATINGS

BACKGROUND OF THE INVENTION

1. Field of the Invention

The present invention relates to shape memory polymers and waterborne coating materials and, more particularly, to waterborne shape memory polymer coatings.

2. Description of the Related Art

Polymeric coating materials are extraordinarily important and used in a wide range of application fields such as building materials, vehicles, household products, beauty products, medical devices, etc., for the purpose of preventing rusting, adding colors, providing additional properties, etc.

Waterborne coating materials, especially waterborne polyurethane (WB-PU)-based coatings are becoming more and more important as a substitution of volatile organic solvent-borne coatings to reduce the volatile organic compounds (VOC) emission to the environment, and are increasingly being used for wood and automobiles as well as softer and/or more flexible materials such as textiles, leather, paper, and rubber.

Waterborne coating materials comprising polymer dispersions are used for various fields like building materials and household products to avoid air pollution and health hazards due to the volatile organic solvents that are also still commonly used for coating materials (as described above). For the dispersibility in water, charging groups are incorporated into the polymer chains. A couple of methods to prepare the aqueous polymer dispersion are known.

Shape memory polymers ("shape memory polymers" or "SMP's") are a class of smart materials that offer mechanical action triggered by an external stimulus. More specifically, SMP's feature large-strain elastic response and extensibility, but temporary shapes can be "stored" through network chain immobilization by vitrification, crystallization or some other means. As a simple example, a complex three dimensional SMP shape can be compacted into a slender form by a cycle of heating to a rubbery state, elastically deforming this rubbery state, cooling to immobilize the network chains, and unloading. Later, application of heat, light, or solvent exposure can "trigger" a return to the equilibrium, complex shape through network chain mobilization.

In terms of macromolecular architecture, SMP's are responsive polymers comprising cross-linked network polymer backbones where the polymer backbones between cross-linking junctions are crystallizable or glassy and can behave as "switching segment." SMP's can be fixed into a deformed temporary shape and later recover to a permanent shape memorized by the cross-linked network structure upon a stimulus, most commonly heat (as discussed above). Generally, SMP's are stiff materials at the shape-fixed state due to the primary mechanism of shape fixing, i.e., crystallization or vitrification of network polymer backbones, and a large force can be generated during the shape recovery.

Paper products are known, particularly absorbent fibrous structure products such as absorbent sanitary tissue paper, including tissue paper provided in roll form such as paper towels or toilet paper, and tissue provided in flat or folded from, such as for facial wipes. Sanitary tissue paper generally comprises absorbent cellulosic fibers, and is generally made in a wet-laid process in which the fibers are provided in an aqueous slurry onto a forming screen or belt, and subsequently dried. Fibrous structures can also be in the form of nonwoven materials comprising polymeric fibers. Nonwoven fibrous structures can be formed by fiber extrusion, or in wet- or dry-laid processes, as is known in the art.

Smart textiles with shape memory effect have attracted much attention in recent decades. It is believed that such smart textiles, including those comprising cellulosic fibers, can memorize their original shape because the cellulose chains are cross-linked and thus the wrinkles on the textiles formed during use can be easily removed after washing without pressing. A variety of cross-linking reactions in the cellulosic fibers have been invented, and most of them utilize volatile and irritant cross-linkers like formaldehyde or ammonium. A great deal of effort and care is required to remove the residues of unreacted cross-linking agents to avoid health hazard.

There is a continuing unmet need for methods providing textile materials with shape memory effect that is relatively long-lasting, reversible, harmless, and which effect can be rendered widely applicable for various substrates.

Further, there is a continuing unmet need for fibrous structures that can retain their shape after use, or beneficially change their shape during use, including after being wetted.

Additionally, there is a continuing unmet need for sanitary tissue products that have built-in shape memory, such that upon wetting, a tissue product can recover a certain amount of shape associated with the built-in shape memory.

Description of the Related Art Section Disclaimer: To the extent that specific publications are discussed above in this Description of the Related Art Section or elsewhere in this Application, these discussions should not be taken as an admission that the discussed publications are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section (as well as throughout the application), they are all hereby incorporated by reference into this document in their respective entirety(ies).

SUMMARY OF THE INVENTION

The present invention recognizes that there are potential problems and/or disadvantages in conventional shape memory textiles, hair shaping methods/coatings, and protective coatings for metal, glass and plastic. For example, there is a need for hair products that allow for rapid styling to curled or straight form. Cottons and linens (fabrics) are comfortable, but difficult to care for due to wrinkles. Also, paper towels are ubiquitous and improvement of water absorbency via shape memory can have a major impact on that industry. Further, in many cases organic solvent-bourne coatings are not desirable for substrates such as textiles and hair (as described above).

In the field of hair care, for example, there are many hair-shaping methods including temporary and permanent methods. As the temporary method, solutions or dispersions of hair-fixative polymers are used in the form of gel, spray, and foam, but the desired effects show relatively short duration and are lost under external influences like combing, wind, high humidity, and contact with water. As the permanent method, a shape of hair is fixed after the use of reduction agents for the cleavage of disulfide bonds in the hair and then the oxidation process for reconnecting the disulfide bonds. This permanent method has long duration of effectiveness, but the chemical treatment of the hair involves an impairment of the structure of the hair. Furthermore, it is not possible to change from one shape of hairdo to another one without troublesome processes.

As another example, smart textiles with shape memory effect have attracted much attention in recent decades. Those textiles, especially comprising cellulosic fibers, memorize their original shape because the cellulose chains are cross-linked in the molecular level and thus the wrinkles on the textiles formed during use can be easily removed after washing without pressing. A variety of cross-linking reactions in the cellulosic fibers have been invented, and most of them utilize volatile and irritant cross-linkers like formaldehyde or ammonium. A great deal of effort and careful is required to remove the residues of unreacted cross-linking agents to avoid health hazard. In addition, the use of this method is limited to cellulosic fibers. A need exists for methods providing such soft materials with shape memory effect of long-lasting, reversible, harmless, and widely applicable for various substrates.

Various embodiments of the present invention may be advantageous in that they may solve or reduce one or more of the potential problems and/or disadvantages discussed above.

It is therefore a principal object and advantage of the present invention to provide a coating technology that utilizes certain SMP chemical compounds/compositions for coating certain substrates (such as those discussed above) in the form of an aqueous dispersion. SMP's that can be applied as coatings from water dispersion are highly desired for a number of commercially relevant applications, including shape memory textiles and protective coatings for metal, glass, and plastic.

It is a further object and advantage of the present invention to provide an aqueous dispersion SMP that can be used in the fabrication of paper towels with shape memory. In accordance with a preferred embodiment, it is important to find the right degree of charge and processing to bind paper fibers in the paper making process. The dispersion particles should be smaller than the diameter of the cellulosic pulp fibers, e.g., of order 1 micron, and possess a net positive charge of sufficient magnitude as to electrostatically adsorb and then bind to the same pulp fibers . . . . In accordance with the foregoing objects and advantages and as described further in the Detailed Description Section herein below, an embodiment of the present invention relates to the novel combination of the concept of SMP's with that of waterborne polymer coatings, i.e., waterborne shape memory polymer coatings. Although many articles have been separately published on shape memory polymers and on waterborne polymer coatings, the combination, that is, waterborne shape memory polymer coating is a novel concept. The SMP's have three main components along the SMP's backbone including (1) switching segment for shape fixing, (2) ionically charged group for water dispersion, and (3) a crosslinkable group for shape memory. As discussed in the Detailed Description Section below, examples of waterborne SMP's have been prepared that when applied to hair from aqueous solution impart shape memory to the hair. Also, batches of waterborne SMP's (both photocrosslinkable and POSS crosslinkable) have been synthesized and proven to work as further described in the Detailed Description Section below.

The waterborne shape memory polymers of an embodiment of the present invention can be added as a coating to most any substrate (e.g., with opposite electrostatic charge) including hair (add shape memory to hair for a solution intermediate between a traditional permanent and daily styling gel), textiles or fabrics (a product that engenders linens and cottons with permanent press qualities for several washes), paper towels (for improved water absorbency and other enhanced performance characteristics) and other fiber based materials imparting a shape memory effect.

In accordance with an embodiment of the present invention, the acetone process is used to prepare an aqueous dispersion of SMP's.

In accordance with an embodiment of the present invention, photo-curable waterborne shape memory polymers and methods of making and using the same are provided.

In accordance with an another embodiment of the present invention, a wide range of industrial and medical applications for the disclosed waterborne shape memory polymers are contemplated; such as temperature sensors and actuators as bulk materials, as well as a self-repairable coating where a scratch can be healed simply by heat.

In accordance with a further embodiment of the present invention, applications that render substrates and fabrics water-sensitive by application of the waterborne SMP coating are contemplated. For such materials, exposure to water vapor or liquid water would trigger a shape change from a temporary state to a permanent shape. Such water-triggered shape change or actuation may find use in household products that dispense material on contact with water, medical products that dispense a drug or other material upon contact with body fluids, or industrial products that cause a desired shape change upon exposure to water as an autonomous control system that protects devices or materials from water without need for a complex water sensor and control electronics.

In accordance with another embodiment of the present invention, utilization of waterborne SMP materials as coatings upon monofilament wires made of metal, polymer, glass, graphite, or ceramic materials is contemplated. In particular, the SMP coating applied from aqueous solution can impart shape memory functionality to such monofilament wires so long as the coating thickness is thick enough to have comparable stiffness with the monofilament core. Applications benefiting from shape memory monofilaments are manifold and can include, but are not limited to: (i) surgical guidewires used in minimally invasive surgeries and wherein shape fixing by medical personnel will allow fine-tuning of guidwire geometry; (ii) fishing line or leader with adaptable shape to suit fishing needs and self-tying knots that are loosely started by the angler and completed with tightening simply by immersion in water; (iii) orthodontic wires whose shape is tuned chair-side, as needed by the orthodontist; (iv) shapeable eye-glass wires; and (v) ornamental wires shaped by an artist.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
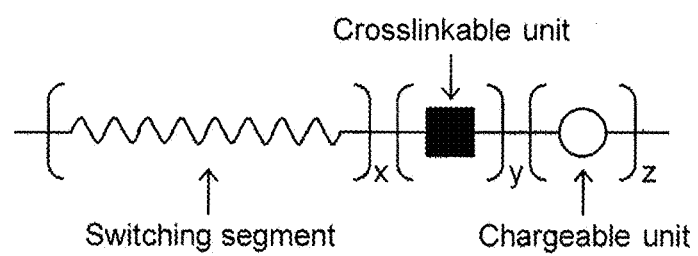
FIG. 1 is a schematic illustration of the chemical structure of a waterborne SMP, according to an embodiment of the present invention.

The present invention will be more fully understood and appreciated by reading the following Detailed Description in conjunction with the accompanying drawings, wherein like reference numerals (if any) refer to like components.

The present invention relates to fibrous structures which comprise as a treatment during manufacture, or after manufacture, a waterborne shape memory polymer (SMP). Unless noted otherwise, all US patents and applications referred to herein are hereby incorporated by reference.

In an embodiment of the present invention the fibrous structure includes a novel combination of the concept of SMP's with that of waterborne polymer coatings, i.e., waterborne shape memory polymer coatings applied to fibrous structures. Although shape memory polymers and waterborne polymer coatings are known, the combination, that is, waterborne shape memory polymer coating is a novel concept. The SMP's have three main components along the SMP's backbone including (1) switching segment for shape fixing, (2) ionically charged group for water dispersion, and (3) a crosslinkable group for shape memory. As discussed below, examples of waterborne SMP's have been prepared that when applied to fibers, such as hair, from an aqueous solution impart shape memory to the hair. Also, batches of waterborne SMP's (both photocrosslinkable and POSS crosslinkable) have been synthesized and proven to work as further described herein.

The waterborne shape memory polymers of an embodiment of the present invention can be added as a coating to the fibrous substrate for improved performance under wet or dry conditions, and other enhanced performance characteristics. For example, a fibrous substrate can have coated thereon an SMP that facilitates imparting a shape memory effect that can serve to cause a texture change upon wetting so that after wetting a fibrous structure such as a paper towel can have a three-dimensional texture for better cleaning performance.

In accordance with an embodiment of the present invention, the acetone process is used to prepare an aqueous dispersion of SMP's.

In accordance with an embodiment of the present invention, photo-curable waterborne shape memory polymers and methods of making and using the same are provided.

In accordance with an another embodiment of the present invention, a wide range of industrial and medical applications for the disclosed waterborne shape memory polymers are contemplated; such as temperature sensors and actuators as bulk materials, as well as a self-repairable coating where a scratch can be healed simply by heat.

In accordance with a further embodiment of the present invention, applications that render fibrous substrates water-sensitive by application of the waterborne SMP coating are contemplated. For such materials, exposure to water vapor or liquid water would trigger a shape change from a temporary state to a permanent shape. Such water-triggered shape change or actuation may find use in household products that dispense material on contact with water, medical products that dispense a drug or other material upon contact with body fluids, or industrial products that cause a desired shape change upon exposure to water as an autonomous control system that protects devices or materials from water without need for a complex water sensor and control electronics.

Definitions

The term "fibrous structure", as used herein, means an arrangement of fibers produced in any papermaking machine known in the art to create a ply of paper. "Fiber" means an elongate particulate having an apparent length greatly exceeding its apparent width. More specifically, and as used herein, fiber refers to such fibers suitable for a papermaking process. Each of the following terms—"fibrous structure" and "fiber"—as used herein expressly excludes natural fabrics, synthetic fabrics, and monofilament wires.

As used herein, "paper product" refers to any wet-formed, fibrous structure product, traditionally, but not necessarily, comprising cellulose fibers. In one embodiment, the paper products of the present invention include tissue-towel paper products, including toilet tissue and paper towels.

A "tissue-towel paper product" refers to paper products comprising absorbent paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include paper towels, toilet tissue (i.e., bath tissue), facial tissue, table napkins, and the like. One embodiment of a method of making tissue-towel paper products is described in U.S. Pat. Nos. 4,529,480 and 4,528,239.

"Ply" or "Plies", as used herein, means an individual fibrous structure or sheet of fibrous structure, optionally to be disposed in a substantially contiguous, face-to-face relationship with other plies, forming a multi-ply fibrous structure. It is also contemplated that a single fibrous structure can effectively form two "plies" or multiple "plies", for example, by being folded on itself. In one embodiment, the ply has an end use as a tissue-towel paper product. A ply may comprise one or more wet-laid layers, air-laid layers, and/or combinations thereof. If more than one layer is used, it is not necessary for each layer to be made from the same fibrous structure. Further, the fibers may or may not be homogenous within a layer. The actual makeup of a tissue paper ply is generally determined by the desired benefits of the final tissue-towel paper product, as would be known to one of skill in the art. The fibrous structure may comprise one or more plies of non-woven materials in addition to the wet-laid and/or air-laid plies.

"Basis Weight", as used herein, is the weight per unit area of a sample reported in lbs/3000 ft2 or g/m2.

"Machine Direction" or "MD", as used herein, means the direction parallel to the flow of the fibrous structure through the papermaking machine and/or product manufacturing equipment.

"Cross Machine Direction" or "CD", as used herein, means the direction perpendicular to the machine direction in the same plane of the fibrous structure and/or fibrous structure product comprising the fibrous structure.

"Sheet Caliper" or "Caliper", as used herein, means the macroscopic thickness of a product sample under load.

"Densified", as used herein, means a portion of a fibrous structure product that exhibits a higher density than another portion of the fibrous structure product.

"Non-densified", as used herein, means a portion of a fibrous structure product that exhibits a lesser density than another portion of the fibrous structure product.

"Bulk Density", as used herein, means the apparent density of an entire fibrous structure product rather than a discrete area thereof.

"Laminating" refers to the process of firmly uniting superimposed layers of paper with or without adhesive, to form a multi-ply sheet.

"Non-naturally occurring" as used herein means that the fiber is not found in nature in that form. In other words, some chemical processing of materials needs to occur in order to obtain the non-naturally occurring fiber. For example, a wood pulp fiber is a naturally occurring fiber; however, if the wood pulp fiber is chemically processed, such as via a lyocell-type process, a solution of cellulose is formed. The solution of cellulose may then be spun into a fiber. Accordingly, this spun fiber would be considered to be a non-naturally occurring fiber since it is not directly obtainable from nature in its present form.

"Naturally occurring fiber" as used herein means that a fiber and/or a material is found in nature in its present form. An example of a naturally occurring fiber is a wood pulp fiber.

In accordance with an embodiment of the present invention, a waterborne shape memory polymer has a chemical structure as shown in FIG. 1, which is synthesizable using a low-molecular-weight polymer chain working as a switching segment, a cross-linkable unit, and a chargeable unit through the general polymerization methods known in the art, such as polyaddition reactions by means by, for example, hydroxyl-isocyanate reaction forming urethane bond, amino-isocyanate reaction forming urea bond, and thiol-ene reaction forming carbon-sulfur bond, and polycondensation reactions by means of, for example, hydroxyl-carboxyl reaction forming ester bond and amino-carboxyl reaction forming amide bond.

As shown, the SMP includes a switching segment, cross-linkable unit, and chargeable unit. The switching segment has a phase transition temperature ($T_{trans}$) like the melting temperature ($T_m$) or the glass transition temperature ($T_g$) above room temperature (RT), preferably 40° C.<$T_{trans}$<80° C. Either semicrystalline polymer or glassy amorphous polymer can be used as the switching segment. Semicrystalline switching segments are low-molecular-weight polymers, for example, poly(ε-caprolactone) (PCL), poly(δ-valerolactone), poly(γ-hydroxybutyrate), poly(β-hydroxybutyrate), poly(β-hydroxypropionate), poly(β-hydroxyoctaonate), poly(L-lactide), poly(D-lactide), poly(glycolide), poly(tetramethylene succinate), poly(trimethylene succinate), poly(ethylene succinate), poly(tetramethylene adipate), poly(trimethylene adipate), poly(ethylene adipate), poly(tetramethylene sebacate), poly(trimethylene sebacate), poly(ethylene sebacate), poly(ethylene oxide), poly(oxymethylene), and their copolymers. Amorphous and glassy switching segments include low-molecular-weight polymers, for example, poly(D,L-lactide), poly(vinyl acetate), poly(methyl methacrylate), poly(methyl acrylate), atactic poly(styrene), and their copolymers. These semicrystalline and amorphous switching segments should be functionalized at the chain ends to incorporate into SMP chain. Functional groups at the chain ends of switching segment are, for example, hydroxyl, carboxyl, amino, mercapto, and vinyl groups.

The cross-linking reaction by means of the cross-linkable unit includes chemical and physical cross-linking. The chemical cross-linking reaction should occur in the bulk state (without solvents) and includes, for example, photo-induced [2+2] cycloaddition reaction which can occur between vinyl groups, between allyl groups, between acryl groups, between styryl groups, between cinnamoyl groups, and between cumarins, photo-induced [4+4] cycloaddition reaction which can occur, for example, between anthracenes, heat-induced [4+2] cycloaddition reaction which can occur between dienes such as 1,3-butadiene, 1,3-cyclopentadiene, furan, and anthracene and dienophiles such as 1,3-cyclopentadiene, maleic anhydride, maleimide, and alkyl acrylate, Menschutkin reaction which can occur between tertiary amines and alkyl halides such as alkyl chloride, alkyl bromide, and alkyl iodide, Huisgen cycloaddition reaction which can occur between 1,3-dipoles such as azides and dipolarophiles such as alkynes. Specific monomers enabling this function include molecules of those functionalities which have two additional functional groups to incorporate into SMP chain, for example, 2-ethyl-2-cinnamoyloxymethyl-1,3-propanediol for photo-induced [2+2] cycloaddition reaction, 1,8-bis(hydroxymethyl)anthracene for photo-induced [4+4] cycloaddition reaction, 2,5-bis(hydroxymethyl)furan and 4-hydroxy-5-(hydroxymethyl)-2(5H)-furanone for heat-induced [4+2] cycloaddition reaction, N-methyldiethanolamine and 2-chloro-1,3-propanediol for Menschutkin reaction, 2-ethynyl-1,3-propanediol and 2-azido-1,3-propanediol for Huisgen cycloaddition reaction. The physical cross-linking includes, for example, hydrogen-bonding, ionic association, and crystallization. Among these physical cross-linking, crystallization is considered to be the most stable cross-linking in a broad temperature range below $T_m$, compared to the other physical cross-linking which are somewhat dynamic and thermally labile. When the crystallization of cross-linkable unit is selected as the physical cross-linking reaction, the melting transition temperature should be higher than that of switching segment.

The chargeable unit includes cationically and anionically chargeable groups. Cationically chargeable groups include, for example, primary, secondary, and tertiary amines. Specific monomers enabling this function include molecules of those functionalities which have two additional functional groups to incorporate into SMP chain, for example, 2-amino-1,3-propanedithiol, 1,6-heptadien-4-amine, bis(2-sulfanylethyl)amine, diallylamine, methyldiallylamine, N,N-bis(2-mercaptoethyl)methylamine, N-methyldiethanolamine and N-methyldipropanolamine. Charging agents which react with and positively ionize those amines are, for example, alkyl halides or acids, preferably relatively weak acids such as glycolic acid and acetic acid. Anionically chargeable groups include, for example, carboxylic acid, sulfonic acid, and phosphoric acid. Specific monomers enabling this function include molecules of those functionalities which have two additional functional groups to incorporate into SMP chain, for example, 2,2-bis(hydroxymethyl)propionic acid, 2,3-dihydroxy-1-propanesulfonic acid, β-glycerophosphoric acid. Charging agents which react with and negatively ionize those acids are, for example, bases, preferably relatively weak bases such as ammonia, diethylamine, and triethylamine.

Advantages of the invention are illustrated by the following Example. However, the particular materials and amounts thereof recited in these examples, as well as other conditions and details, are to be interpreted to apply broadly in the art and should not be construed to unduly restrict or limit the invention in any way.

Example 1

Figure 2A:
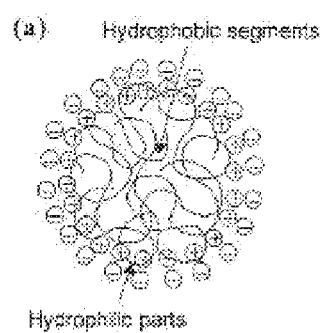
FIG. 2(a) is a schematic illustration of the anticipated structure of SMP nano- or micro particle dispersed in water, according to an embodiment of the present invention.
Figure 2B:
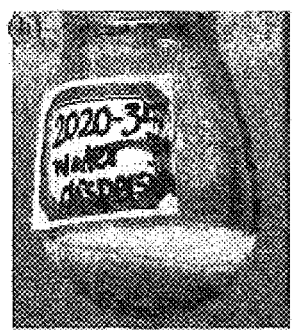
FIG. 2(b) is a photograph of an aqueous SMP dispersion, according to an embodiment of the present invention.

This Example describes the aqueous dispersion of SMP, which can be prepared by means of a general method like the acetone process. In the acetone process, the uncharged SMP is reacted with a charging agent in the acetone solution (1-10 w/v %) with stirring at 25-50° C. for 1-10 hours, and preheated deionized water is added into the solution dropwise with stirring at 45-60° C. Then acetone is evaporated at 65-75° C. with stirring or rotovapped at 25-60° C. The concentration of resulting aqueous dispersion can be reduced (for adjustment) by rotovapping. FIG. 2 (a) illustrates the anticipated structure of nano- or micro-particle of SMP dispersed in water. The hydrophobic segments are considered to be surrounded by the charged units so that the SMP can disperse in water, as shown in FIG. 2 (b).

Figure 3:
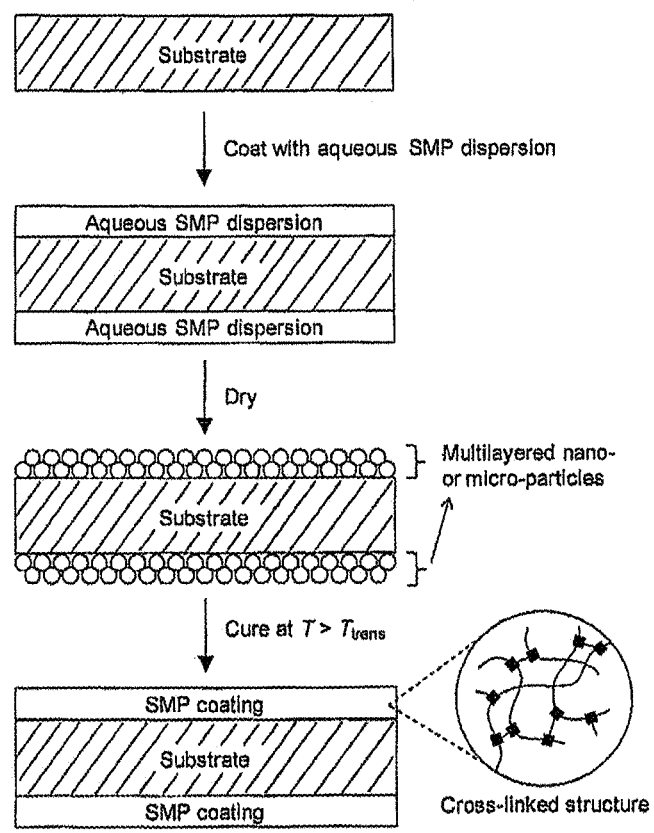
FIG. 3 is a cross-sectional schematic illustration of coating procedure using aqueous SMP dispersion, according to an embodiment of the present invention.

The aqueous SMP dispersion can be used to coat the substrates according to the procedure shown in FIG. 3. After the coating of the substrate with the aqueous SMP dispersion, the coating is dried and multilayered SMP particles remain on the substrate. To prepare a homogeneous coating layer, the SMP coating is heated above $T_{trans}$, and then to set the permanent shape a treatment like high temperature or UV irradiation is applied to form the cross-linked structure.

Figure 4:
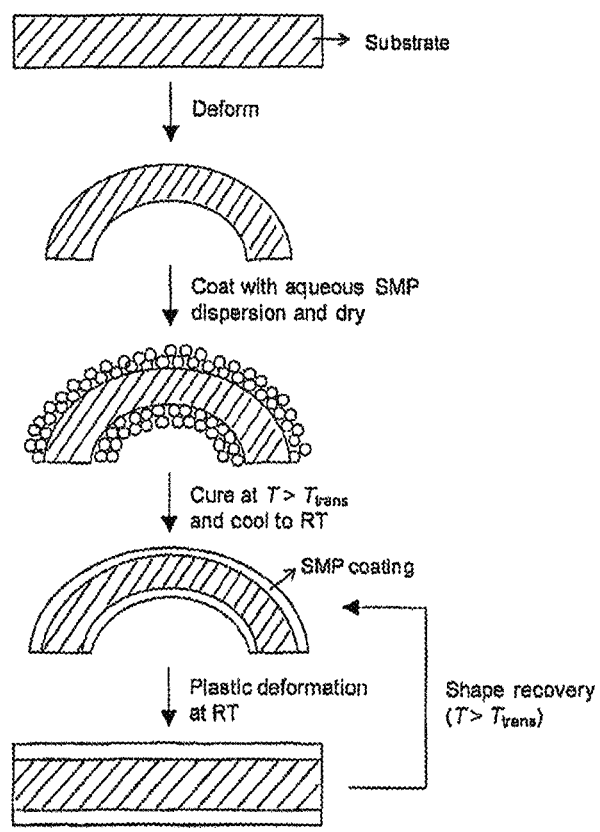
FIG. 4 is a cross-sectional schematic illustration of shape memory behavior of SMP-coated substrates, according to an embodiment of the present invention.

The waterborne shape memory polymer coating is applicable to various application fields like hair care and shape memory textile in which the permanent shape of substrate often should be different from the original shape of the substrate itself. Thus, the coating procedure also can be modified as shown in FIG. 4.

First, the substrate is deformed, and then coated with the aqueous SMP dispersion. After by drying and curing (cross-linking), a deformed permanent shape is prepared. The shape memory ability is examined also as shown in FIG. 4. The SMP-coated substrate is deformed at room temperature by means of plastic deformation of SMP-coating layer. The shape recovery is carried out by heating the SMP-coated substrate.

Based on the protocol described above, two different SMP's were synthesized and found to be dispersible in water. One is thermoplastic polyurethanes (PU) synthesized from PCL diol (switching segment), 2-ethyl-2-cinnamoyloxymethyl-1,3-propanediol (ECMPD, cross-linkable unit), N-methyldiethanolamine (NMDEA, chargeable unit), and 1,6-hexanediisocyanate (HDI) with general tin catalyst like dibutyltin dilaurate (DBTDL), and the other one is thermoplastic polyurethanes produced from PCL diol, POSS diol (such as TMP DiolIsobutyl POSS®, 1,2-PropanediolIsobutyl POSS®, and trans-CyclohexanediolIsobutyl POSS® purchased from Hybrid Plastics), NMDEA, and HDI with DBTDL.

Figure 5:
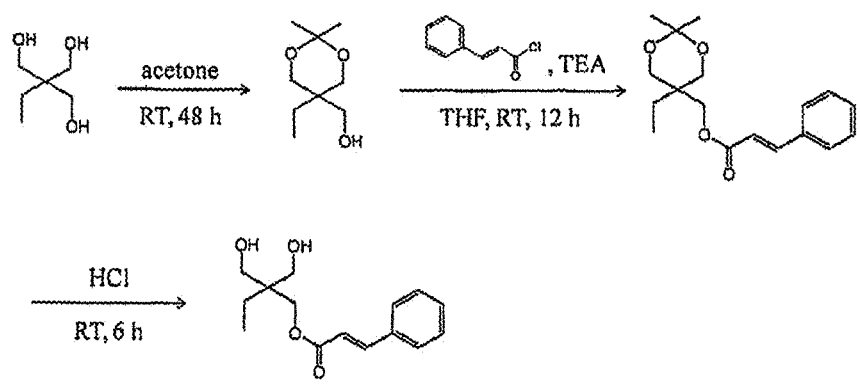
FIG. 5 is a schematic illustration showing the synthesis of 2-ethyl-2-cinnamoyloxymethyl-1,3-propanediol (ECMPD), according to an embodiment of the present invention.
Figure 6:
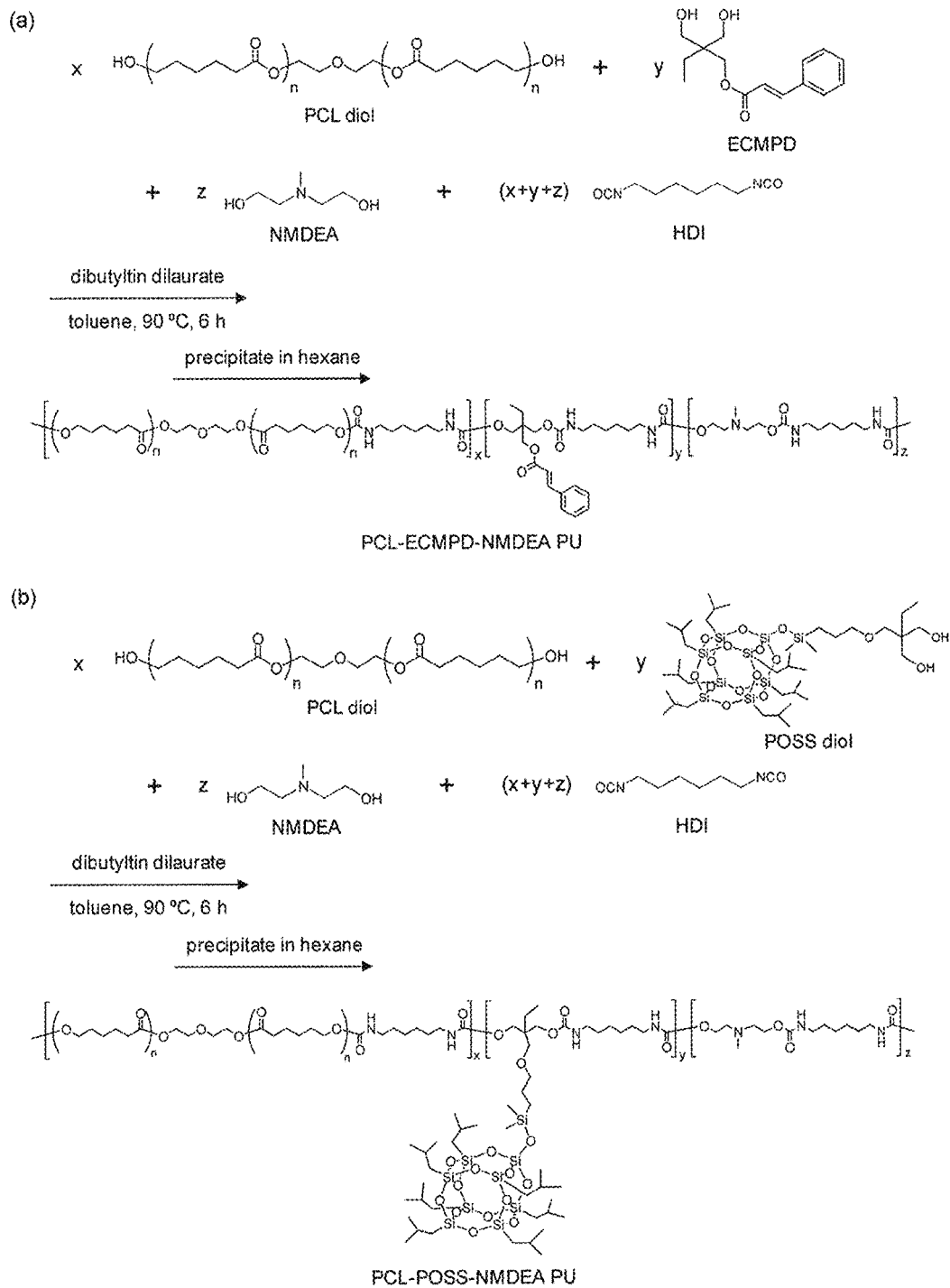
FIG. 6 is a schematic illustration showing the synthetic procedures of: (a) PCL-ECMPD-NMDEA PU and (b) PCL-POSS-NMDEA PU, according to an embodiment of the present invention.
Figure 7:
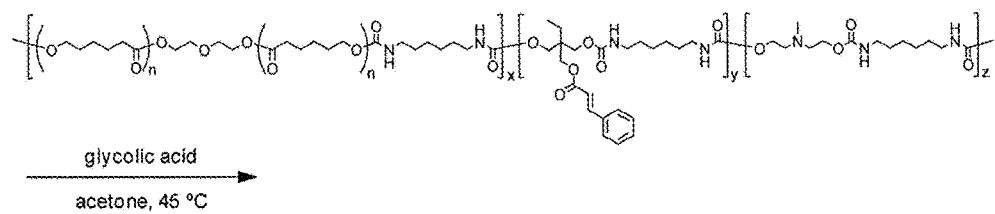
FIG. 7 is a schematic illustration showing a quaternization reaction using: (a) glycolic acid for PCL-ECMPD-NMDEA PU and (b) PCL-POSS-NMDEA PU, according to an embodiment of the present invention.
Figure 7:
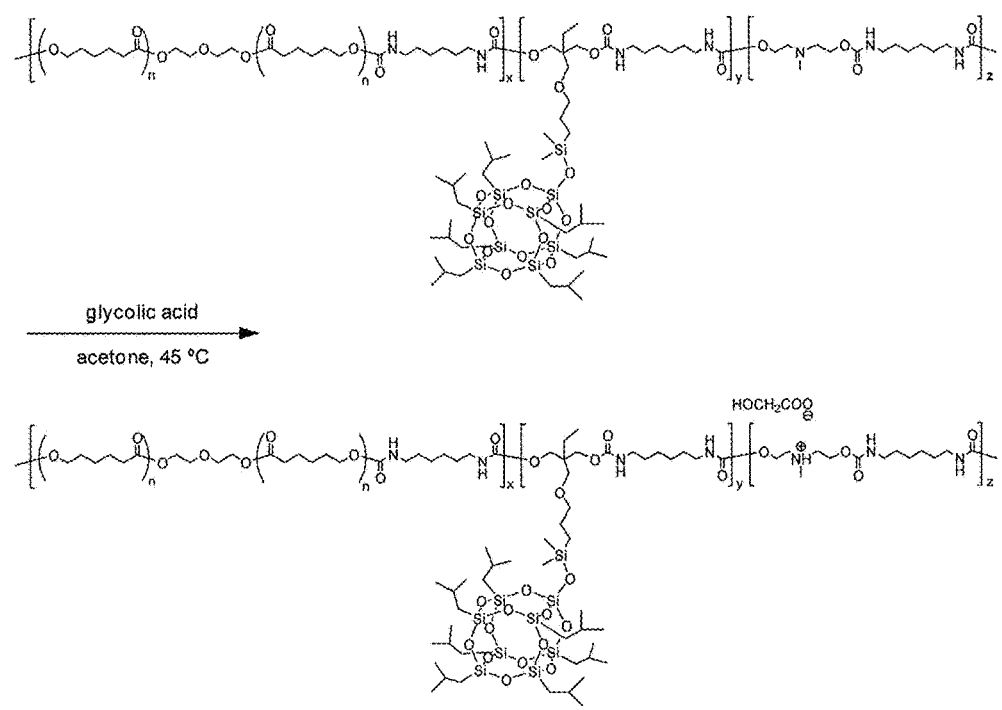

Before the polyurethane synthesis, ECMPD was synthesized as shown in FIG. 5. The synthetic procedures of the first (UV-curable) and second (heat-curable) types of waterborne SMP's are shown in FIGS. 6 (a) and (b), respectively. FIG. 6 is a schematic illustration showing the synthetic procedures of: (a) PCLECMPD-NMDEA PU and (b) PCL-POSS-NMDEA PU, according to embodiments of the present invention. In both cases, polyurethanes are formed by the reaction of oligomeric diols (soft segments), small molecule diols (chain extenders), and a diisocyanate to in a solvent with tin catalyst. Following polymerization, the polymer is purified and isolated from the solvent and unreacted components by precipitation, filtration, and drying. After the synthesis, these PU's were cationized (quaternized) by the reaction of tertiary amine in NMDEA unit with glycolic acid as shown in FIG. 7, and aqueous dispersions (FIG. 2 (b)) were prepared by means of the acetone process. FIG. 7 is a schematic illustration showing a quaternization reaction using: (a) glycolic acid for PCL-ECMPD-NMDEA PU and (b) PCL-POSS-NMDEA PU, according to embodiments of the present invention. In both cases, polyurethanes charged to cationic form (quaternized) by treatment with glycolic acid in solution.

Figure 8:
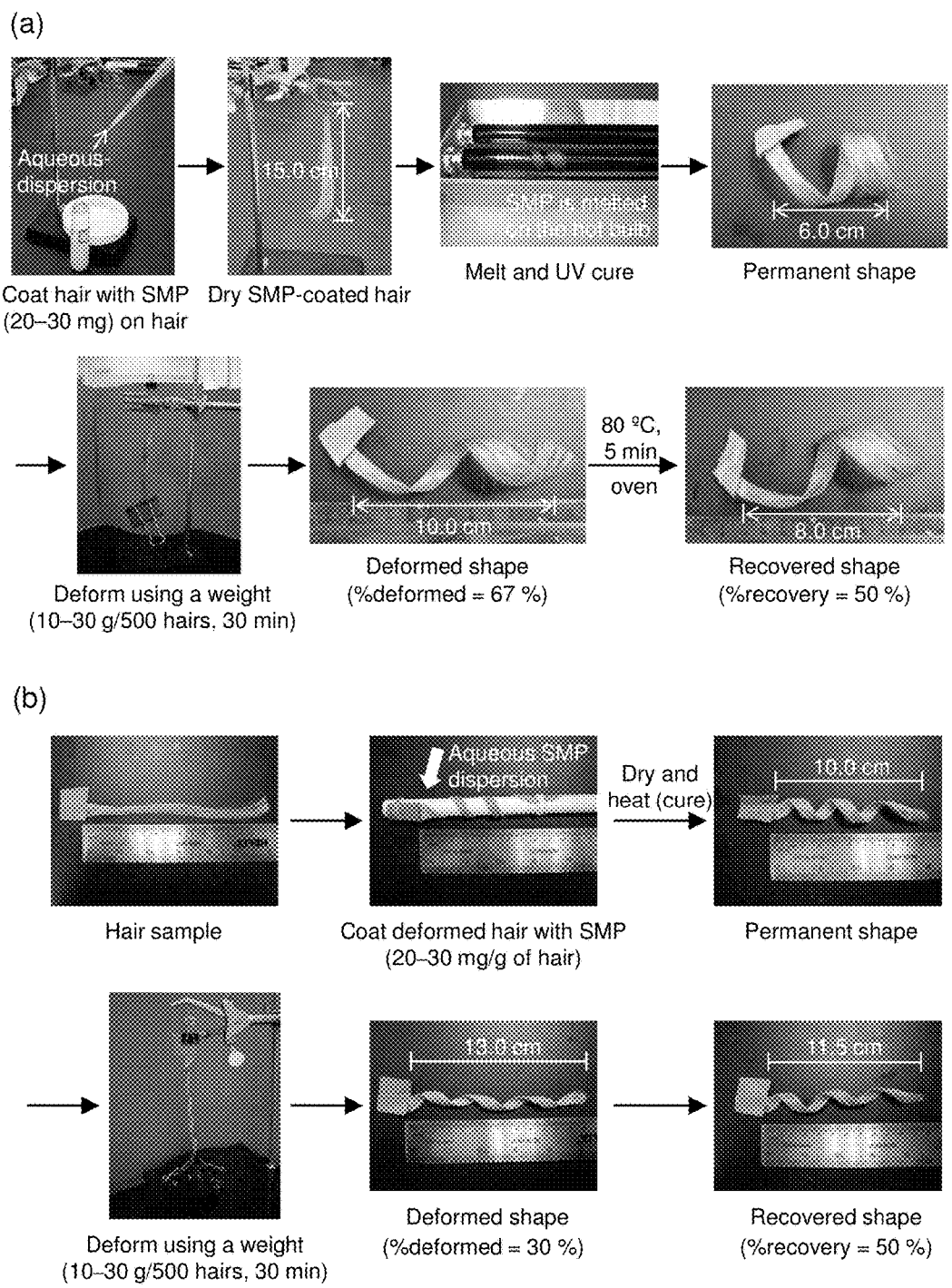
FIG. 8 shows images of a shape memory experiment of SMP-coated hairs using: (a) PCL-ECMPD-NMDEA PU and (b) PCL-POSS-NMDEA PU, according to an embodiment of the present invention.

The aqueous SMP dispersions were used to coat the hairs as shown in FIG. 8. The shape memory procedure was carried out according to the procedure shown in FIG. 4.

The deformation and the recovery were estimated using the hair length shown in FIG. 8 and the following equations.

$$\% \text{ Deformed} = \frac{(L_{deform} - L_{original})}{L_{original}} * 100$$

$$\% \text{ Recovery} = \frac{(L_{deformed} - L_{Recovered})}{(L_{deformed} - L_{original})} * 100$$

As a result, both of the systems of UV-curable and heat-curable WB-SMP coated hairs exhibited approximately 50% recovery from the deformed shape. Depending on the amount of WB-SMP coating and the composition of cross-linkable unit and chargeable unit, the recovery varied in the range of 20-80%.

The results show that the preparation of the aqueous dispersions of shape memory polymers containing UV-curable or heat-curable compositions, and the exhibition of the good shape memory properties of SMP-coated hairs was successful. It is contemplated that the same success can be applied to a SMP-coated textile system.

Advantages of the invention are also illustrated by the following additional Examples. However, the particular materials and amounts thereof recited in these examples, as well as other conditions and details, are to be interpreted to apply broadly in the art and should not be construed to unduly restrict or limit the invention in any way.

Figure 9:
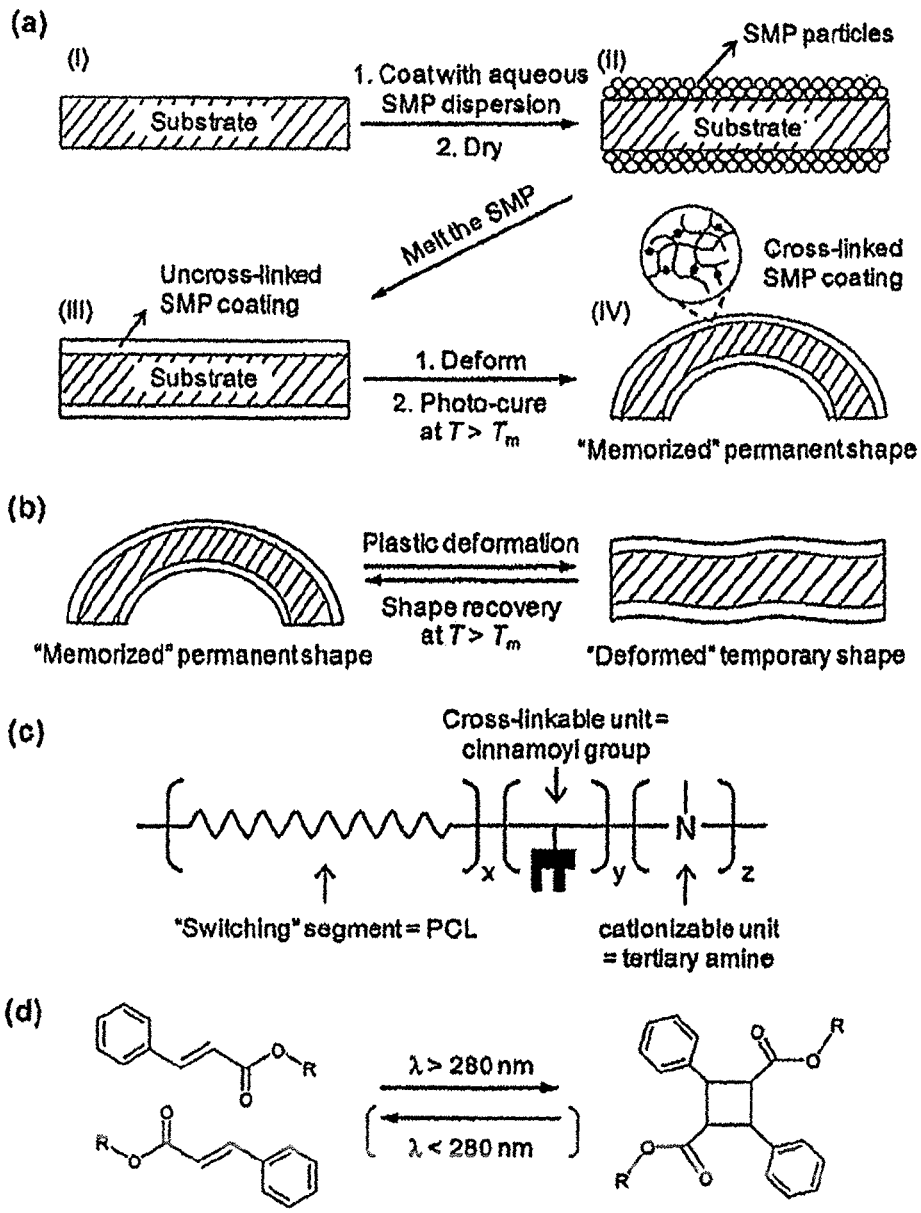
FIG. 9 is a schematic illustration showing (a) the procedure for preparation of SMP-coated substrate with a "memorized" permanent shape, (b) shape memory behavior of SMP-coated substrate, and (c) formulation of waterborne SMP. Scheme of photo-reversible dimerization reaction of cinnamoyl groups is also shown (d), according to an embodiment of the present invention.

In the Examples below, waterborne polyurethane (WB-PU) based coatings and a SMP coating are combined to create waterborne shape memory polyurethane coating (see FIG. 9). As further discussed below, to prepare SMP coating layer with cross-linking structure on the substrates using WB-PU, a cross-linking reaction should be performed after the coating of the substrates with WB-PU. Dimerization of cinnamic acid in the presence of UV light is well-known and widely used to prepare cross-linked polymeric materials because of no need of catalyst, no by-product, reversibility, and the facile controllability. Typically cinnamic acid can be dimerized by the irradiation of UV light with a wavelength of >280 nm, and dissociated with that of <280 nm. The reaction feature of cinnamic acid is very useful as discussed herein, especially to make the cross-linking structure after the formation of thin PU layer on the substrates; the PU can be cross-linked by UV cure. It is also noted that the dissociation ability of cinnamic acid can potentially add the removability to SMP coating from the substrates.

As described further below, a series of WB-thermoplastic PU's (TPU's) containing poly(ε-caprolactone) (PCL) as a switching segment, cinnamoyl-functionalized unit, and ion-containing unit is prepared. To use hairs as a model substrate, a cation-containing unit is used. This yields good adhesion of WB-TPU's onto hairs which have negative changes near the surface. Effects of chemical composition and sequence structure of the building blocks on the dispersibility in water, thermal properties, and cross-linking reaction kinetics have been examined. Furthermore, shape memory behavior of WB-SMP-coated hairs is demonstrated.

Materials

The following materials were used in the following Examples. 1,1,1-tri(hydroxymethyl)propane (TMP), p-toluene sulfonic acid (p-TSA), potassium carbonate ($K_2CO_3$), cinnamoyl chloride, triethylamine (TEA), anhydrous magnesium sulfate ($MgSO_4$), ε-caprolactone (ε-CL), stannous octoate ($Sn(Oct)_2$), N-methyldiethanolamine (NMDEA), 1,6-hexanediisocyanate (HDI), dibutyltin dilaurate (DBTDL, 95%), and glycolic acid (GA) were purchased from Sigma-Aldrich and used as received. Concentrated hydrochloric acid (HCl), acetone, tetrahydrofuran (THF), methanol, dichloromethane (DCM), diethyl ether, and toluene were purchased from Fisher Scientific. TEA and toluene were distilled with calcium hydride. Poly(ϵrolactone) diols (PCL diols) with number-average molecular weights of 2,600 and 3,600 were purchased from Scientific Polymer Product, Inc. and used as received.

Analytical Procedures

The following analytical procedures were used in the following Examples. $^1$H NMR spectra were recorded with 300 MHz Bruker Spectrospin 300 spectrometer with chloroform-d solutions at room temperature. Gel permeation chromatography (GPC) was performed with Waters GPC system equipped with two 30 cm ResiPore columns (Polymer Laboratories, Inc.), Waters 2414 Refractive Index Detector, and a Wyatt miniDAWN TREOS multi-angle laser light scattering apparatus. Differential scanning calorimetry (DSC) was carried out with TA Q200 in the temperature range from −80° C. to 150° C. at a heating and cooling rate of 10° C./min and −10° C./min, respectively. Fourier-Transformed Infrared spectroscopy (FT-IR) was performed using a Perkin Elmer Spectrum One FT-IR spectrometer. Scanning electron microscopy (SEM) images were taken using JEOL JSM-5600 SEM. Dynamic light scattering (DLS) was conducted at 25° C. using Malvern Zeta-sizer Nano ZS to determine the average particle sizes of aqueous PU dispersions.

EXAMPLES

Example 2

Synthesis of 2-ethyl-2-cinnamoyloxymethyl-1,3-propanediol (ECMPD)

Figure 10:
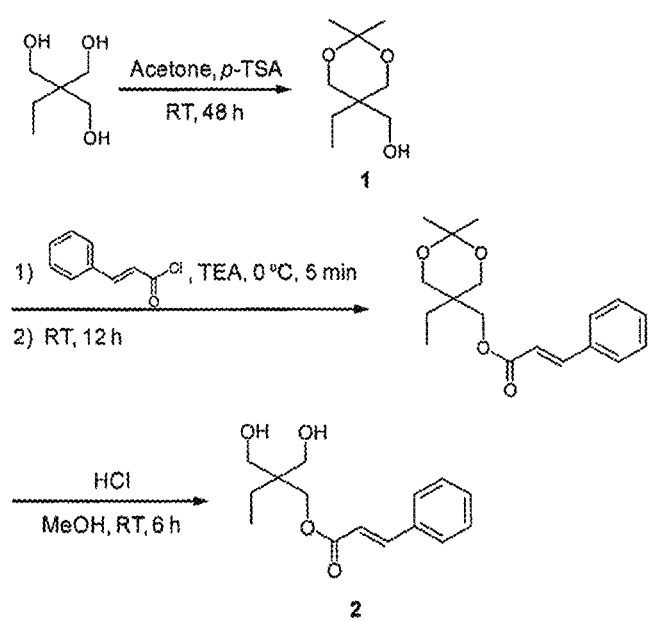
FIG. 10 is a schematic illustration showing the synthesis of 2-ethyl-2-cinnamoyloxymethyl-1,3-propanediol (EC-MPD, 2), according to an embodiment of the present invention.

This Example describes the synthesis of 2-ethyl-2-cinnamoyloxymethyl-1,3-propanediol (ECMPD). TMP (50 g), acetone (300 mL), and p-TSA (50 mg) were introduced into a 500 mL round-bottom flask. The mixture was stirred for 2 days at room temperature. The solution was neutralized by adding 1.25 g of $K_2CO_3$, filtered, and evaporated with rotoevaporation. The remained material was dissolved in DCM and the solution was purified by extraction with water three times. The DCM layer was dried with $MgSO_4$, and rotovapped. The remained viscous liquid was dried under vacuum at room temperature for 2 days to give the product 1 (44 g, 67%, FIG. 10). To a 500 mL round-bottom flask were introduced 40.0 g (0.2295 mol) of 1, 38.24 g (0.2295 mol) of cinnamoyl chloride, and 300 mL of dried THF.

The reaction mixture was stirred at 0° C. for 5 min. Then 32 mL (0.2295 mol) of TEA was added dropwise to the flask. After the addition, the reaction mixture was stirred at room temperature for 12 h. Then the by-product, triethylamine hydrochloride (TEA-HCl) was filtered off and the filtrate was rotovapped to obtain 5-ethyl-5-cinnamoyloxymethyl-2,2-dimethyl-1,3-dioxane. The obtained 5-ethyl-5-cinnamoyloxymethyl-2,2-dimethyl-1,3-dioxane was dissolved in methanol (350 mL), and then concentrated HCl (33 mL, 0.40 mol) was added dropwise to the solution at room temperature with stirring.

After the continuous stirring for 6 h, the reaction mixture was cooled down in an ice bath and TEA (55.7 mL, 0.40 mol) was added to the mixture. After the evaporation of methanol, the remained material was dissolved in DCM and insoluble by-product (TEA-HCl) was filtered off. Then the filtrate was extracted with water three times, and the organic layer was dried with $MgSO_4$, and rotovapped. The crude product was recrystallized from diethyl ether solution to obtain the product, 2-ethyl-2-cinnamoyloxymethyl-1,3-propanediol (ECMPD, 2, 15.7 g, 15.9%) as a white crystal.

Example 3

Synthesis of $PCL_{ECMPD}$ Diol

Figure 11:
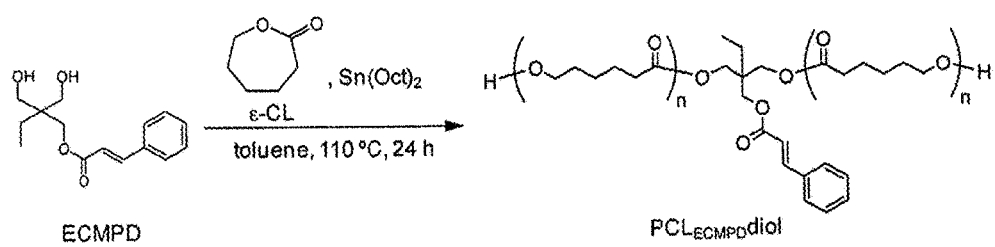
FIG. 11 is a schematic illustration showing the synthesis of $PCL_{ECMPD}$ diol, according to an embodiment of the present invention.

This example describes the synthesis of $PCL_{ECMPD}$ diol (see FIG. 11).

ECMPD (0.772 g, 2.92 mmol) was introduced into a 100 mL Airfree round-bottom flask and the system was nitrogen-purged. And then ε-CL (10.0 g, 87.6 mmol) and 2 mL of toluene solution of $Sn(Oct)_2$ (47 mg, 0.117 mmol) were added to the flask. The reaction mixture was stirred at 110° C. for 24 h.

After that, the resulting polymer solution was diluted using THF, and the polymer product was precipitated in 300 mL of ice-cooled methanol, and dried under vacuum at room temperature for at least 2 days (yield: 91%).

Example 4

Synthesis of Thermoplastic Polyurethanes (TPU's)

This example describes the synthesis of thermoplastic polyurethanes (TPU's).

In brief, three types of thermoplastic polyurethanes (types I, II, and III) were synthesized. Syntheses and characterization of PCL-ECMPD-NMDEA PU (one-step synthesis, type I), PCL-ECMPD-NMDEA PU (two-step synthesis, type II), and $PCL_{ECMPD}$-NMDEA PU (type III) (FIG. 12a-c and Table 1), are described below.

Figure 12:
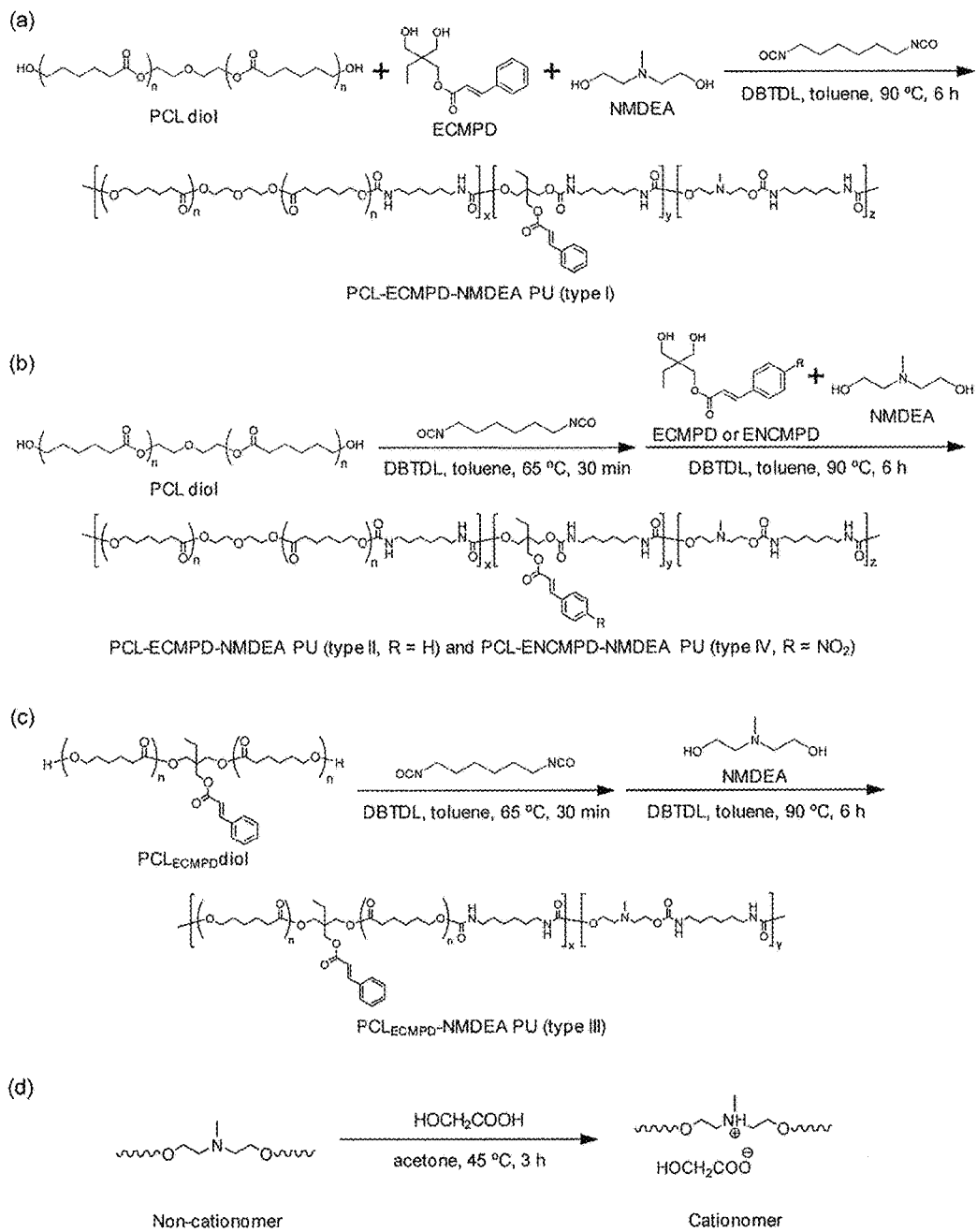
FIG. 12 is a schematic illustration showing (a) One-step synthesis of PCL-ECMPD-NMDEA PU (type I); (b) Two-step syntheses of PCL-ECMPD-NMDEA PU (type II) and PCL-ENCMPD-NMDEA PU (type IV); (c) Two-step synthesis of $PCL_{ECMPD}$-NMDEA PU (type III); and (d) Synthesis of PU cationomers using glycolic acid, according to an embodiment of the present invention.

Types I and II TPU's were synthesized using PCL diols, ECMPD, NMDEA, and HDI in toluene solution. Type III was synthesized with $PCL_{ECMPD}$ diols, NMDEA, and HDI in toluene solution. For all the reactions, DBTDL (0.02 equiv. of HDI) was used as a catalyst. The difference between types I and II lies in the different polymerization procedure; type I was synthesized by one-step polymerization where all of the reagents were introduced into a 100 mL Airfree round-bottom flask at the same time and the polymerization was performed at 90° C. for 6 h (FIG. 12a). Type II was obtained by two-step polymerization where PCL diol reacted first with HDI at 65° C. for 20 min to make PCL functionalized with isocyanate groups at the chain ends and then a mixture of ECMPD and NMDEA was added as chain extenders and the chain extension reaction (polymerization) was conducted at 90° C. for 6 h (FIG. 12b). For Types III, a similar procedure as that for type II was adopted (FIG. 12c) where NMDEA was used as a chain extender. For all the types, resulting polymers were precipitated in 300 mL hexane and dried under vacuum at room temperature for at least 2 days.

Table 1 is shown below.

TABLE 1

Synthesis and Characterization of Photo-curable PU's Containing PCL, ECMPD, and NMDEA.

| Type | Sample | Feed (actual$^a$) molar ratio | Yield (%) | $M_n^b$ | PDI$^c$ | Weight content (wt. %)$^a$ PCL | ECMPD | NMDEA |
|---|---|---|---|---|---|---|---|---|
| I | | PCL3.6k/ECMPD/NMDEA | | | | | | |
| | I-1 | 1.0 (1.0)/1.0 (0.7)/1.0 (0.6) | 91 | 26700 | 1.1 | 85.4 | 4.5 | 1.6 |
| | I-2 | 1.0 (1.0)/2.0 (1.4)/1.0 (0.6) | 87 | 32800 | 1.1 | 79.8 | 8.3 | 1.5 |
| | I-3 | 1.0 (1.0)/2.0 (1.4)/2.0 (1.2) | 93 | 13200 | 1.5 | 76.6 | 7.9 | 3.0 |
| II | | PCL3.6k/ECMPD/NMDEA | | | | | | |
| | II-1 | 1.0 (1.0)/1.5 (1.1)/2.0 (1.5) | 97 | 26100 | 1.2 | 77.1 | 6.3 | 3.7 |
| | II-2 | 1.0 (1.0)/2.0 (1.6)/1.0 (0.5) | 94 | 25100 | 1.3 | 78.3 | 8.9 | 1.3 |
| | | PCL2.6k/ECMPD/NMDEA | | | | | | |
| | II-3 | 1.0 (1.0)/2.0 (1.4)/2.0 (1.3) | 95 | 23600 | 1.2 | 68.8 | 10.1 | 4.0 |
| III | | PCL$_{ECMPD}$3.9k/NMDEA | | | | | | |
| | III-1 | 1.0 (1.0)/2.0 (1.7) | 93 | 32000 | 1.2 | 80.0$^e$ | 5.7$^e$ | 4.3 |
| | III-2 | 1.0 (1.0)/3.0 (2.7) | | 31000 | 1.2 | 75.3$^e$ | 5.4$^e$ | 6.5 |

$^a$Determined based on $^1$H-NMR.
$^{b,c}$Number-average molecular weight (b) and polydispersity index (c) determined based on GPC.

Example 5

Preparation of Aqueous Dispersions of TPU Cationomers

This example describes the preparation of aqueous dispersions of TPU cationomers with glycolic acid and dispersibility in water (see Table 2, below).

In brief, a TPU sample was dissolved in acetone to prepare 1%, 2%, 5% or 10% (w/v) solution in 250 mL round-bottom flask. Then glycolic acid (GA, 1.0 equiv. of NMDEA unit) was added and dissolved. The reaction solution was stirred at 45° C. for 3 h for the quaternization reaction to form TPU cationomer (FIG. 12d). After that, pre-heated distilled water (similar volume with acetone) was added dropwise with vigorous stirring. During the addition of water, the solution became turbid due to the formation of polymer micelles. The TPU dispersion in the acetone/water mixed solvent was then stirred at 70° C. until acetone was removed to form 1%, 2%, 5%, or 10% (w/v) aqueous TPU dispersion. In some cases, a portion of polymers was precipitated during the addition of DI water, and the precipitate was removed from the aqueous dispersion. To coat hair samples, 1% aqueous dispersion was condensed to 10% by rotovap.

The results show that the weight content of NMDEA is important (TPU's having more than 3% NMDEA showed 100% dispersibility (no precipitate) even in 10% aqueous dispersion). All the samples exhibited good dispersion in water through the acetone process using 1% solution.

Table 2 is shown below.

TABLE 2

Dispersibility of PU cationomers in water.

| Type | Sample | Concentration in acetone (w/v %)$^a$ | Dispersed content (wt. %)$^b$ | Particle size (nm)$^c$ |
|---|---|---|---|---|
| I | I-1 | 10 | 60 | N.D.$^d$ |
| | | 1 | 100 | N.D. |
| | I-3 | 1 | 100 | N.D. |
| II | II-1 | 10 | 90 | 392$^e$ |
| | | 5 | 90 | N.D. |
| | | 1 | 100 | 474 |
| | II-2 | 10 | 20 | 448$^e$ |
| | | 5 | 60 | N.D. |
| | | 2 | 60 | N.D. |
| | | 1 | 100 | 795 |
| | II-3 | 10 | 100 | N.D. |
| | | 2 | 100 | 686 |
| III | III-1 | 10 | 100 | N.D. |
| | | 1 | 100 | N.D. |
| | III-2 | 2 | 90 | 1140$^e$ |
| | | 1 | 100 | N.D. |

$^a$Concentration of PU cationomer in acetone solution.
$^b$Calculated using the equation of (dispersed PU content, wt. %) = (mass of dispersed PU)/{(mass of dispersed PU) + (mass of precipitated PU)} × 100.
$^c$Averaged particle size determined by dynamic light scattering.
$^d$Not determined.
$^e$Measured for dispersed component.

Figure 13:
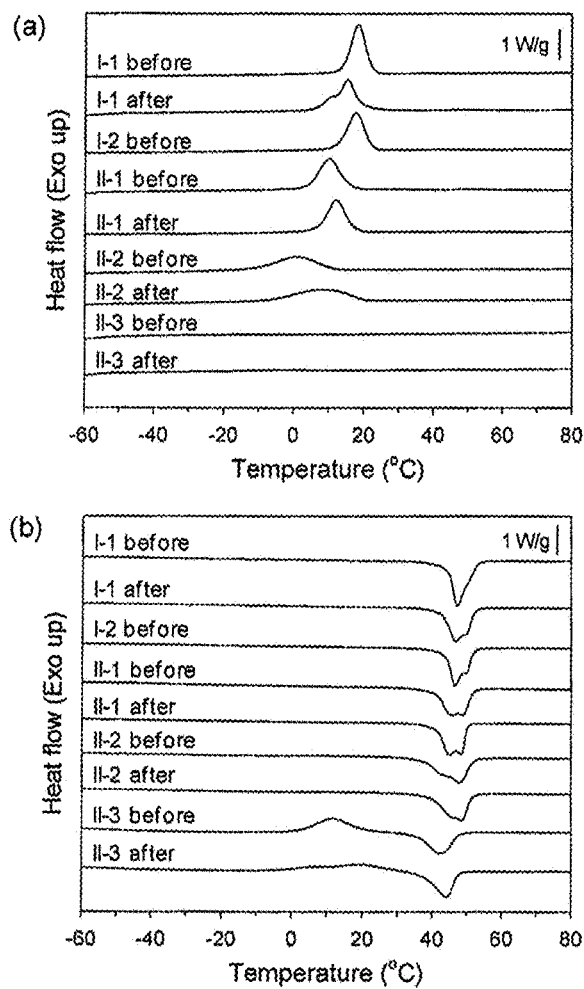
FIG. 13 is a graphical illustration showing DSC curves during the cooling scan (−10° C./min, a) and the 2nd heating scan (10° C./min, b) for samples I-1, I-2, II-1, II-2, and II-3 before and after the quaternization reaction, according to an embodiment of the present invention.

For thermal properties of non-cationomer and cationomers, see FIG. 13 and Table 3 (below). Crystallization kinetics (important for shape fixing at room temperature) was significantly affected by the PCL chain length, ECMPD and NMDEA unit contents, and sequence structure (with an increase in ECMPD and NMDEA content, the PCL crystallization rate decreased). The presence of ionic groups (in cationomers) tended to cause slight increase of crystallization kinetics for samples I and II, presumably because the ionic aggregation caused enhanced nucleation. For samples III, the chain mobility restriction by the ionic aggregates seems to be stronger because, in those cationomers, cinnamoyl groups and quaternary ammonium cations are separated and so ionic groups can be more closely packed in ionic aggregates, which resulted in slightly retarded crystallization kinetics.

Table 3 is shown below.

TABLE 3

Thermal properties of PCL-ECMPD-NMDEA PU's (types I and II)
before and after the quaternization reaction determined based on DSC.

| Type | Sample | | $T_{mc}$ (°C.)[a] | $\Delta H_{mc}$ (J/g)[b] | $T_{cc}$ (°C.)[c] | $\Delta H_{cc}$ (J/g)[d] | $T_m$ (°C.)[e] | $\Delta H_m$ (J/g)[f] | $T_g$ (°C.)[g] |
|---|---|---|---|---|---|---|---|---|---|
| I | I-1 | before[h] | 18 | 53 | —[j] | — | 47 | 51 | −40 |
| | | after[i] | 15 | 48 | — | — | 47, 50 | 50 | −42 |
| | I-2 | before | 18 | 47 | — | — | 47, 50 | 45 | −30 |
| | | after | N.D.[k] | N.D. | — | — | N.D. | N.D. | N.D. |
| | I-3 | before | 5 | 47 | — | — | 43, 49 | 53 | −26 |
| | | after | 15 | 46 | — | — | 45, 49 | 47 | −14 |
| II | II-1 | before | 10 | 47 | — | — | 46, 49 | 49 | −29 |
| | | after | 12 | 47 | — | — | 45, 49 | 48 | −28 |
| | II-2 | before | 0 | 41 | — | — | 43, 48 | 48 | −34 |
| | | after | 8 | 41 | — | — | 45, 48 | 47 | −30 |
| | II-3 | before | −27 | 3 | 12 | 33 | 43 | 36 | −46 |
| | | after | −3 | 4 | 20 | 26 | 44 | 34 | −49 |
| III | III-1 | before | 13 | 54 | — | — | 41, 45 | 53 | −43 |
| | | after | 11 | 51 | — | — | 41, 45 | 52 | −51 |
| | III-2 | before | 9 | 49 | — | — | 39, 44 | 49 | −40 |
| | | after | −4 | 43 | — | — | 37, 44 | 47 | −40 |

[a,b]Temperature (a) and heat (b) of melt-crystallization during the cooling scan.
[c,d]Temperature (c) and heat (d) of cold-crystallization during the 2nd heating scan.
[e,f]Temperature (e) and heat (f) of melting during the 2nd heating scan.
[g]Glass transition temperature.
[h,i]Before (h) and after (i) the quarternization reaction.
[j]Not observed.
[k]Not determined.

Example 6

Measurement of Photo-Dimerization Reaction Kinetics

Figure 14:
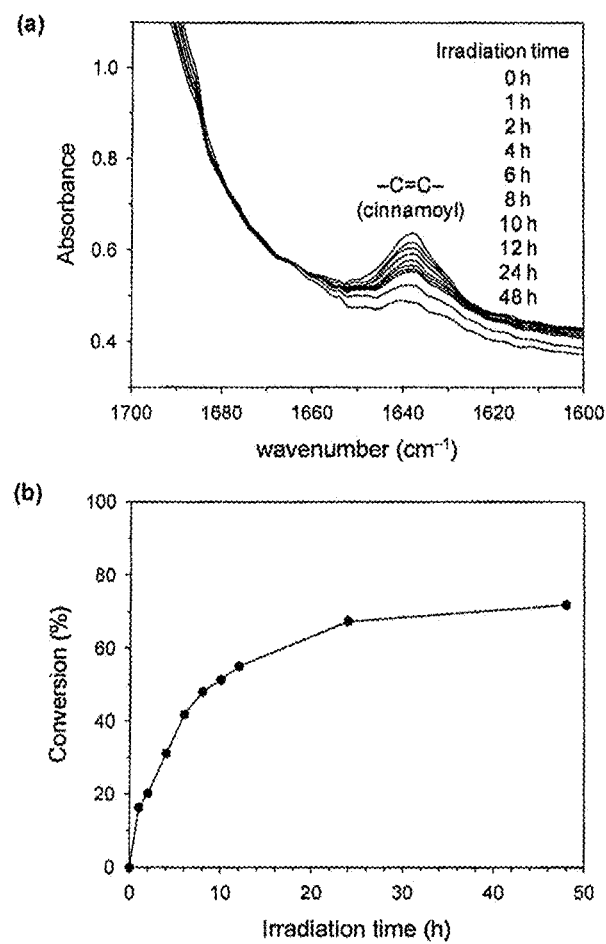
FIG. 14 is a graphical illustration showing time courses of (a) FT-IR spectra in the region of —C═C— stretching vibration of cinnamoyl group in sample I-2 (non-cationomer) during the UV irradiation (peak emission: λ=352 nm, 2 mW/cm$^2$ at 365 nm) at 60° C.; and (b) chemical conversion of the photo-dimerization reaction calculated using the FT-IR data shown in (a), according to an embodiment of the present invention.
Figure 15:
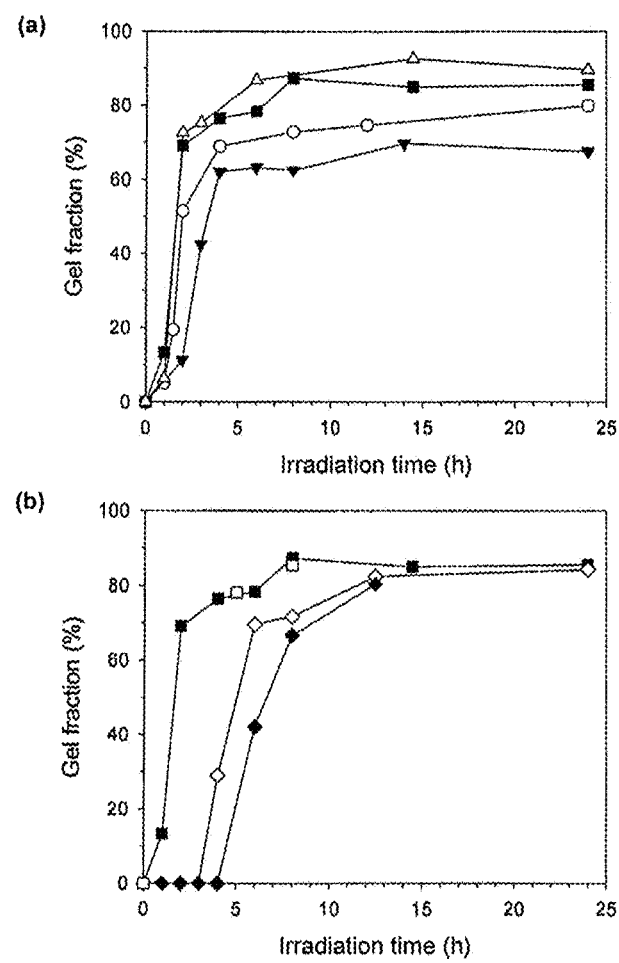
FIG. 15 is a graphical illustration showing Gel fraction change for PU coating (types I and II, thickness: 20 μm) on a glass slide during the UV irradiation (peak emission: λ=352 nm, 2 mW/cm$^2$ at 365 nm), where (a) shows a comparison among non-PU cationomer samples of I-1 (▼), I-2 (○), II-1 (■), and II-3 (Δ). Temperature was kept at 70° C. during the UV irradiation, and (b) shows a comparison between non-cationomer (■ and □) and cationomer (♦ and ◊) of II-1. Temperature was 70° C. (solid symbols) or 80° C. (open symbols), according to an embodiment of the present invention.

This example describes the measurement of photo-dimerication reaction kinetics. UV absorption spectra change (FIG. 14) and gel fraction change (FIG. 15) due to dimerization reaction of cinnamate groups during the UV irradiation was studied to examine the kinetics of cross-linking reaction.

To study the reaction kinetics of photo-dimerization of cinnamoyl moieties in the TPU samples described above, the time course of FT-IR spectra was measured for a thin TPU layer (thickness: ~20 μm) on a KBr disk during the UV irradiation (black light, peak emission: 352 nm, ~2.0 mW/cm² at 365 nm) at 60° C. The thin TPU layer was deposited from THF solution and dried under vacuum at room temperature prior to use.

The results show UV spectra change verified that the UV irradiation resulted in the dimerization reaction of cinnamoyl moieties. PCL-ECMPD-NMDEA PU (type II, two-step synthesis) showed higher gel fraction at equilibrium than PCL-ECMPD-NMDEA PU (type I, one-step) probably due to more periodic ECMPD sequence which seems to have resulted in more efficient interchain cross-linking reaction rather than intrachain reaction. Furthermore, type II exhibited higher cross-linking kinetics (reached the equilibrium in 2 h) than type I (4 h was needed for the equilibrium). The presence of ionic groups in cationomers resulted in notably slower cross-linking reaction due to the interchain ionic association (physical crosslinks) restricting the polymer chain mobility.

Example 7

Measurement of Cross-Linking Reaction Kinetics and Coating of Hair Samples with TPU Cationomers This example describes the measurement of cross-linking reaction kinetics and coating of hair samples with TPU cationomers.

To study the cross-linking reaction kinetics for the TPU samples, thin TPU layers (thickness: ~20 μm) were prepared on glass slides by sandwiching 100 μL of THF solution (0.3 g/mL) with a portion of two glass slides and sliding the two substrates against each other. The obtained TPU layers were dried under vacuum at room temperature for 1 day. The cross-linking reaction was carried out by UV irradiation (black light, peak emission: 352 nm, ~2.0 mW/cm² at 365 nm) at 70° C. or 80° C. After the UV cure, soluble components of the thin TPU layer were carefully washed out with THF, and the remained material was dried under vacuum at room temperature for 1 day. Gel fraction values were calculated using the weights of TPU layer before and after the UV cure.

Hair tresses (~500 hairs, length: 15 cm) provided by P&G were used as a model substrate to study the ability of TPU cationomer layer to add the shape memory property to substrates. First, 10% (w/v) aqueous dispersion of TPU cationomer was added drop-wise onto the hair tress (20-30 mg, TPU cationomer/g, hair). After being dried in the hood, the TPU-coated hair tress was completely dried under vacuum at room temperature. And then the samples were heated at 80° C. for 15 min to melt the TPU cationomer and form a homogeneous coating.

Figure 16:
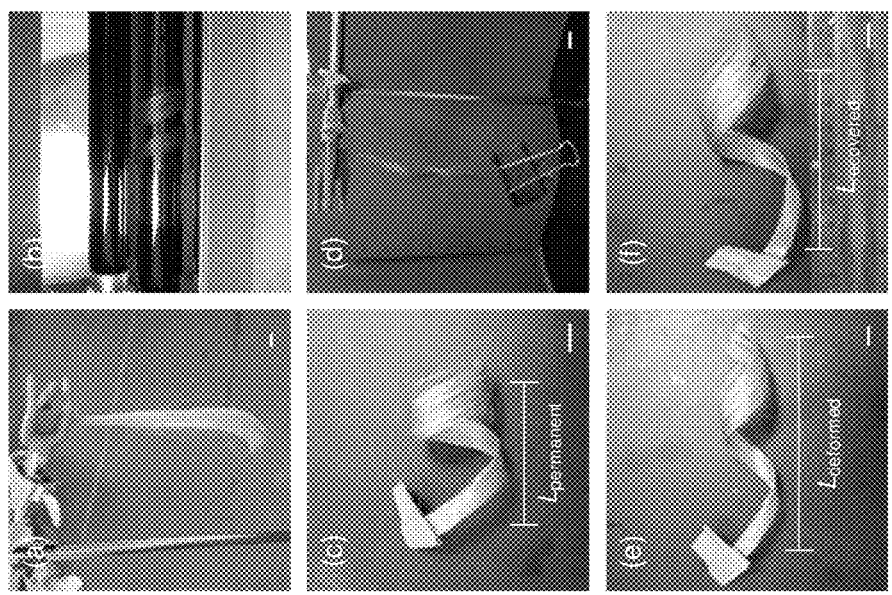
FIG. 16 shows SEM photographs of (a) hairs, (b) shampoo-washed hairs, (c) PU cationomer (II-2)-coated hairs (as-coated), (d) PU-cationomer (II-2)-coated hairs (melted), according to an embodiment to the present invention.

The morphology (SEM) of hairs and SMP coated hairs is shown in FIG. 16. The SEM image of "as-coated" sample verified the particle size of ~1 μm which is much smaller than hair diameter, and good to make a thin SMP layer.

Figure 17:
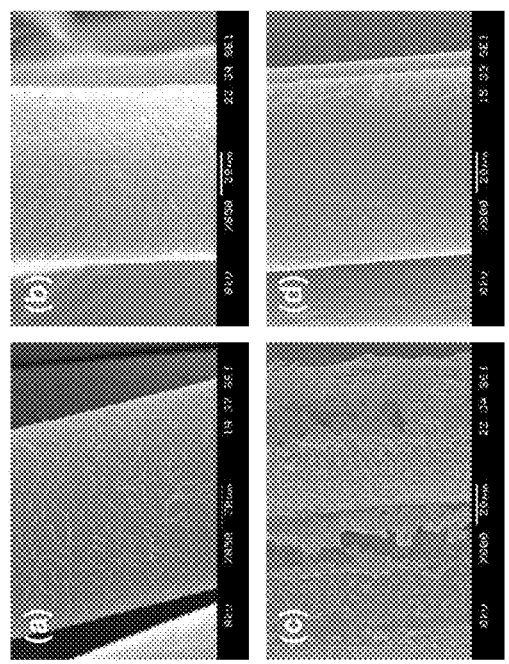
FIG. 17 shows photographs shape memory behavior of PU cationomer (II-2)-coated hair: (a) PU cationomer (II-2)-coated hair tress (approx. 500 hairs, length=15 cm); (b) "memorized" curled permanent shape; (c) deformed shape obtained by plastic deformation; and (d) "recovered" curled shape, according to an embodiment to the present invention. The scale bar represents 10 mm.

Demonstration of shape memory property of SMP-coated hairs is shown in FIG. 17. The SMP-coated hair tress showed good shape fixing and shape recovery.

According to the above-referenced Examples, a photo-curable waterborne shape memory polymer coating was created. The effects of chemical composition and sequence structure of the multi-block polyurethanes on the dispersibility in water, thermal properties, and cross-linking reaction kinetics were extensively examined to optimize those parameters. The facile applicability of the photo-curable WB-SMP was exhibited.

Example 8

This Example describes water-triggered waterborne shape memory polymer coatings, according to an embodiment of the present invention. This Example contemplates applications that require films or fabrics with water-sensitivity that is engendered by application of the waterborne SMP coating. For such articles, exposure to water vapor or liquid water would trigger a shape change from a temporary state to a permanent shape. This will require the switching segment (FIG. 1) of the polymers in the waterborne SMP of an embodiment of the present invention to be water soluble or water-swellable so that the fixed state can give way to the permanent shape by water, which will re-mobilize those network chains. This water-triggered shape change or actuation may find use in: (a) household products that dispense material on contact with water, (b) medical products that dispense a drug or other material upon contact with body fluids, or (c) industrial products that cause a desired shape change upon exposure to water as an autonomous control system that protects devices or materials from water without need for a complex water sensor and control electronics.

A prophetic example of reducing this concept to actual practice is described herein. Polymers with poly(ethylene glycol) (PEG) soft segments of varying molecular weight and with hard segments containing POSS or a photocrosslinkable group described above is synthesized. After charging positively with glycolic acid, the acetone process is used to disperse the polymers in water and then the dispersion is applied to fibrous structures, including paper structures, or fabrics of different types (for example natural fibers like cotton) and dried. A temporarily wrinkled state is prepared by heating and compressing in a mold and then cooled to fix this shape. Finally, the coated fabric is exposed to water vapor or liquid water to measure the degree of recovery to the equilibrium shape.

Example 9

This Example describes utilization of the waterborne SMP materials of an embodiment of the present invention as coatings upon monofilament wires made of metal, polymer, glass, graphite, or ceramic materials. In particular, the SMP coating applied from aqueous solution can impart shape memory functionality to such monofilament wires. In a preferable embodiment, the coating thickness is thick enough to have comparable stiffness with the monofilament core. Applications benefiting from shape memory monofilaments are manifold and include: (a) surgical guide-wires used in minimally invasive surgeries and wherein shape fixing by medical personnel will allow fine-tuning of guide-wire geometry; (b) fishing line or leader with adaptable shape to suit fishing needs and self-tying knots that are loosely started by the angler and completed with tightening simply by immersion in water; (c) orthodontic wires whose shape is tuned chair-side, as needed by the orthodontist; (d) shapeable eye-glass wires; and (e) ornamental wires shaped by the artist.

A prophetic example of reducing this concept to actual practice is described herein. In brief, sample wire (for example fishing line) is primed with a negative charge using a surfactant or corona exposure, followed by dipping in or conveyance through a trough of dispersion at a concentration between 1% and 10%. This will ensue until a range of coating thicknesses is achieved for a set of samples. After drying and heating above the hard-block Tm to erase processing history, the coatings are crosslinked by further application of heat or by exposure to UV light (depending on the nature of the polymer as described in the invention). This crosslinking is done in the shape of mechanical equilibrium (no stress) for the wire or in a deformed state, such as spiraled, bent, or twisted. Then, a temporary fixed shape is formed by heating, deforming, and cooling. The quality of fixing will be observed after removing force at room temperature and recorded as the percentage of the applied deformation that is retained upon release of the deforming forces. Finally, the coated wires are heated (or exposed to water) to reveal the degree of shape recovery, recorded as the percentage of return from the fixed shape to the permanent shape.

Figure 18:
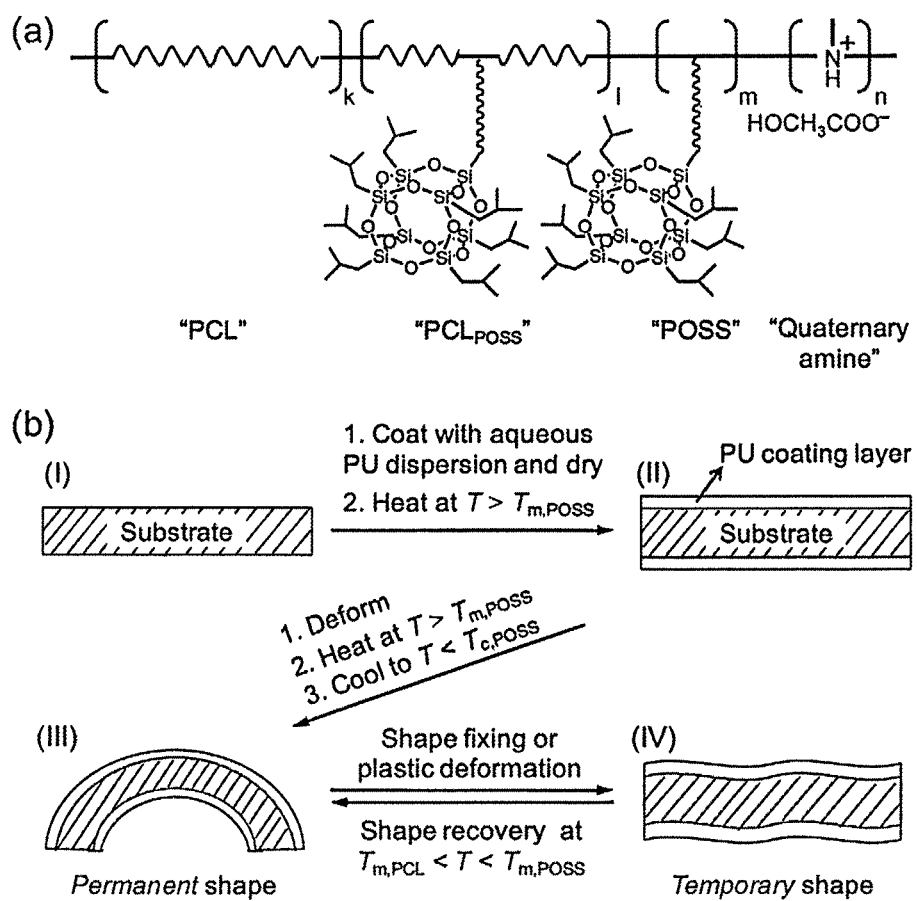
FIG. 18 is a schematic illustration showing (a) formulation of multi-component waterborne shape memory polyurethanes containing PCL-, $PCL_{POSS}$-, POSS-, and quaternary amine-units, and (b) procedure of preparing SMP-coated substrate with a permanent shape as well as a temporary shape (I-IV), and shape memory behavior between them (III and IV), according to an emobodiment of the present invention.

The next set of Examples describes the use of multi-component waterborne shape memory polyurethanes (SM-PU) containing poly($\epsilon$-caprolactone) [PCL], $PCL_{POSS}$ with PCL chains tethered to a single POSS, POSS, and quaternary amine units to coat flexible substrates including fibrous paper and human hairs (see FIG. 18(*a*)). Shape memory behavior of the SM-PU-coated flexible substrates with shape change between permanent and temporary shapes was examined (see FIG. 18(*b*)).

The materials used include, but are not limited to, the following: $\epsilon$-Caprolactone ($\epsilon$-CL, 97%), stannous octoate ($Sn(Oct)_2$, 95%), N-methyldiethanolamine (NMDEA, ≥99%), hexamethylene diisocyanate (HDI, ≥99%), dibutyl-tin dilaurate (DBTDL, 95%), and glycolic acid (GA, 99%) were purchased from Sigma-Aldrich. (3-(2,2-Bis(hydroxymethyl)butoxy) propyl)dimethylsiloxy-3,5,7,9,11,13, 15-isobutylpentacyclo[$9.5.1.1^{3,9}.1^{5,15}.1^{7,13}$]octasiloxane and 1-(3-(2,3-dihydroxypropyl)oxy)propyl-3,5,7,9,11,13, 15-isobutylpentacyclo[$9.5.1.1^{3,9}.1^{5,15}.1^{7,13}$]octasiloxane, hereafter referred to as POSS1 diol and POSS2 diol, respectively, were purchased from Hybrid Plastics. Acetone, tetrahydrofuran (THF), methanol, and toluene were purchased from Fisher Scientific. All of the materials shown above except for $\epsilon$-CL, NMDEA, and toluene were used as received. $\epsilon$-CL and toluene were purified by distillation with calcium hydride. NMDEA was dried using a hand-made column filled with molecular sieves (pore size: ~4 Å). Poly($\epsilon$-caprolactone) diol (PCL diol) with the number-average molecular weight ($M_n$) of ~3,000 were purchased from Scientific Polymer Products, Inc. (Ontario, N.Y., USA) and used as received. $^1$H NMR was used to determine $M_n$ value ($M_{n,NMR}$) and degree of polymerization (x) for the commercial PCL diol: $M_{n,NMR}$=3,600 and x=31. It is noted that diethylene glycol was used as an initiator to produce the commercial PCL diol according to the manufacture. Paper used as a flexible substrate for waterborne SMP coating and SM experimentation was obtained from Toyo Corporation, under the brand name Flower Paper (Tokyo, JAPAN), and used as received. Hair tresses used as a flexible substrate for waterborne SMP coating and SM experimentation were kindly supplied by Procter and Gamble and used following procedures outlined herein.

The analytical materials used include, but are not limited to, the following: $^1$H NMR spectra were recorded with 300 MHz Bruker Spectrospin 300 spectrometer using chloroform-d solutions at room temperature. The $M_n$, weight-average molecular weight ($M_w$), and polydispersity index (PDI) were determined with gel permeation chromatography (GPC) equipped with two 30 cm ResiPore columns (Polymer Laboratories Inc., USA), Waters 2414 Refractive Index Detector, and a Wyatt miniDAWN TREOS multi-angle laser light scattering apparatus using THF solutions at 40° C. Differential scanning calorimetry (DSC) measurements were carried out with TA Instruments Q200 under a nitrogen atmosphere in a temperature range from −85° C. to 140° C. (or 150° C.) at a heating and a cooling rate of 10° C.·min$^{-1}$ and −10° C.·min$^{-1}$, respectively. Wide-angle X-ray scattering (WAXS) measurements were carried out at room temperature using Rigaku S-MAX3000 operated at 45 kV and 0.88 mA with a Cu-Kα source (λ=1.5405 Å) in transmission mode. Dynamic mechanical analysis (DMA) was performed with TA Instruments Q800 in tensile mode with an oscillation frequency of 1 Hz in a temperature range from −80° C. to 150° C. at a heating rate of 2° C.·min$^{-1}$.

Example 10

Synthesis of PCL$_{POSS1(or\ 2)}$ Diol

Figure 24:
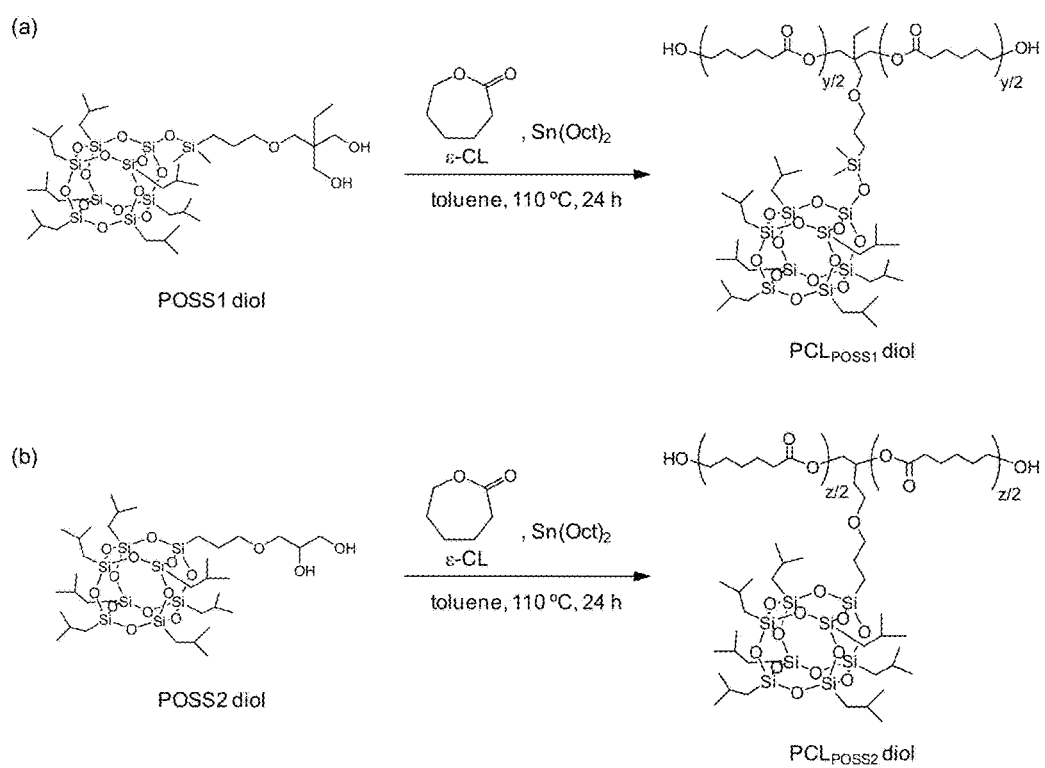
FIG. 24 is a schematic illustration showing synthesis of (a) $PCL_{POSS1}$ diol and (b) $PCL_{POSS2}$ diol, according to an embodiment of the present invention.

This Example describes the synthesis of PCL$_{POSS1(or\ 2)}$ diol. In order to synthesize the waterborne SM-PU, PCL$_{POSS}$ diols were first synthesized as shown in FIG. 24. Two different POSS diols ("TMP DiolIsobutyl POSS®" and "1,2-PropanediolIsobutyl POSS®", hereafter referred to POSS1 diol and POSS2 diol, respectively) were used as initiators for the ring-opening polymerization of ε-caprolactone to prepare PCL$_{POSS1}$ diol and PCL$_{POSS2}$ diol.

In brief, for the synthesis of PCL$_{POSS1}$ diol, POSS1 diol (3.112 g, 2.92 mmol) was introduced into a 100 mL Airfree round-bottom flask (ChemGlass) and the system was filled with dry nitrogen gas. Toluene (4 mL) was added into the flask to dissolve POSS1 diol. Then ε-CL (10.0 g, 2.92×30 mmol=87.61 mmol) and 0.5 mL of toluene solution of Sn(Oct)$_2$ (47 mg, 0.117 mmol) were added to the flask. The reaction mixture was stirred at 110° C. for 24 h. After that, the resulting polymer solution was slightly diluted with THF, and the polymer product was precipitated in 300 mL of ice-cooled methanol, filtered, and dried under vacuum at room temperature overnight. Then, the polymer product was dissolved again in THF, precipitated in 300 mL of cold hexane in a dry ice/acetone bath, filtered, and dried under vacuum at 40° C. for 1 day and at room temperature for at least 2 days. $^1$H NMR: degree of polymerization (y)=31 and $M_{n,NMR}$=4,600. GPC: $M_{n,GPC}$=4,500 and PDI=1.9.

For the synthesis of PCL$_{POSS2}$ diol, the same procedure as that for PCL$_{POSS1}$ diol was employed except using POSS2 diol instead of POSS1 diol. $^1$H NMR: degree of polymerization (z)=33 and $M_{n,NMR}$=4,700. GPC: $M_{n,GPC}$=5,800 and PDI=1.2.

Example 11

Synthesis of Multi-Component Polyurethanes

Figure 25:
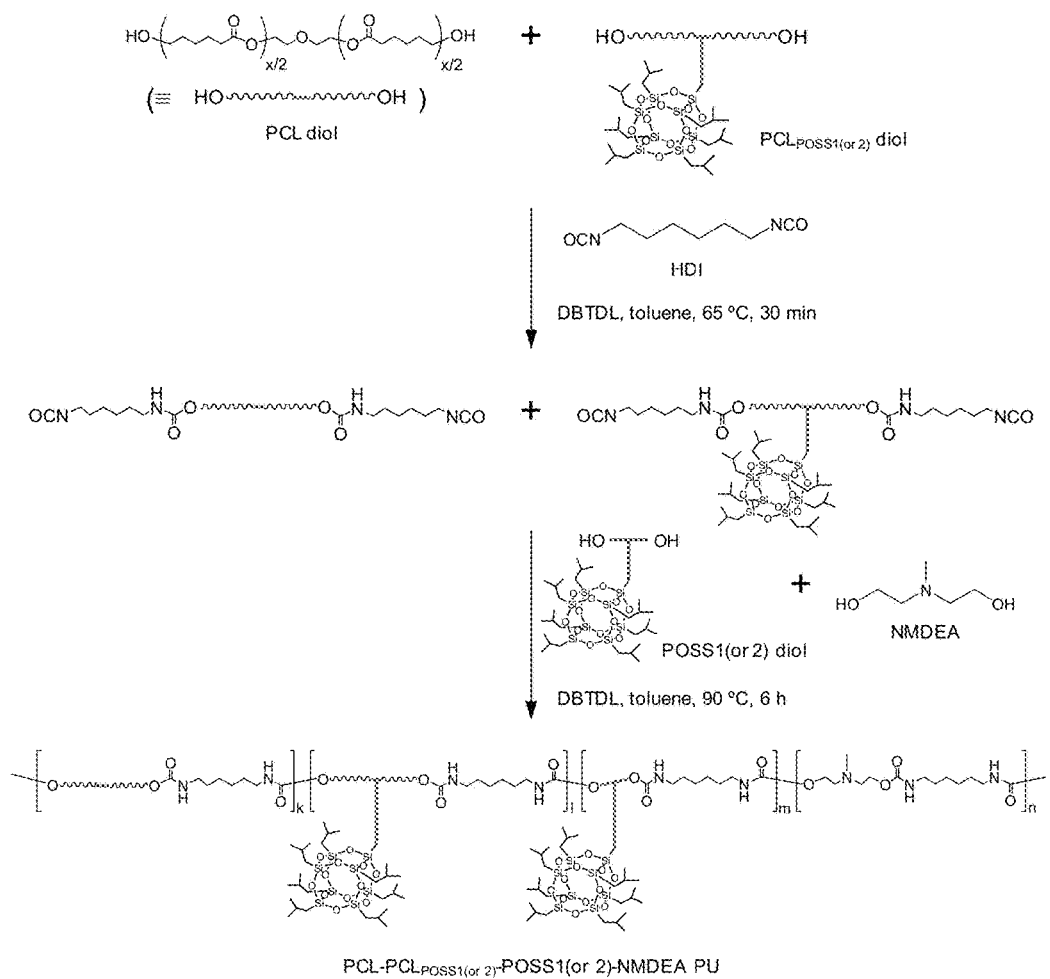
FIG. 25 is a schematic illustration showing synthesis of PCL-$PCL_{POSS1(or\ 2)}$-POSS1 (or 2)-NMDEA PU, according to an embodiment of the present invention.

This Example describes the synthesis of two types of polyurethanes containing PCL, PCL$_{POSS1}$, POSS1, and NMDEA-units (type 1) and those containing PCL, PCL$_{POSS2}$, POSS2, and NMDEA-units (type 2) by a two-step polymerization using PCL diol and PCL$_{POSS1(or\ 2)}$ diol as "polyols" and POSS1(or 2) diol (as described in the previous Example) and NMDEA as chain extenders in the presence of hexamethylene diisocyanate (HDI) and tin catalyst (see FIG. 25). The feed molar ratio of [PCL diol+PCL$_{POSS1(or\ 2)}$ diol]:POSS diol:NMDEA was set to 1.0:1.5:2.0 (except for sample 1b) or 1.0:0.75:2.0 (for sample 1b). The feed molar ratio of PCL diol:PCL$_{POSS1(or\ 2)}$ diol was 1:0, 1:1, or 0:1.

In brief, two types of multi-component PU (types 1 and 2) were synthesized through the two-step reaction. The difference between syntheses of types 1 and 2 lies in the use of different types of POSS; PCL$_{POSS1}$ diol and POSS1 diol for type 1 and PCL$_{POSS2}$ diol and POSS2 diol for type 2. Those PU's were obtained using PCL diol, PCL$_{POSS1(or\ 2)}$ diol, POSS1(or 2) diol, NMDEA, HDI, and DBTDL.

First, a mixture of PCL diol and PCL$_{POSS1(or\ 2)}$ diol with a predetermined molar ratio (1:0, 1:1, or 0:1) was dissolved in toluene (~60%, w/v) under a nitrogen atmosphere at 65° C. in a 100 mL Airfree round-bottom flask. Then, a toluene solution of HDI (an equimolar amount of PCL diol+PCL$_{POSS1(or\ 2)}$ diol+POSS1(or 2) diol+NMDEA) and that of DBTDL (0.02 equiv. of HDI) were added into the reaction mixture drop-wise (the concentration of PCL diol+PCL$_{POSS1(or\ 2)}$ diol was diluted to ~45%, w/v), and the reaction solution was stirred at 65° C. for 30 min to make PCL and PCL$_{POSS1(or\ 2)}$ functionalized with isocyanate groups (NCO) at the chain ends (OCN-PCL-NCO and OCN-PCL$_{POSS1(or\ 2)}$-NCO).

After that, a toluene solution of POSS1(or 2) diol and NMDEA was added drop-wise (the concentration of OCN-PCL-NCO+OCN-PCL$_{POSS1(or\ 2)}$-NCO was diluted to ~30%, w/v) and the reaction solution was stirred at 90° C. for 6 h for polymerization. The resulting polymer was precipitated in a large excess volume of hexane in a dry ice/acetone cooling bath, filtered, and dried under vacuum at 50° C. for 1 day and at room temperature for 2 days. Yields of all the samples were in the range from 69% to 87%.

A total of four type 1 PU's and two type 2 PU's with different sequence structures, different POSS-types, and different weight contents of PCL, PCL$_{POSS}$, POSS, and NMDEA-units, but similar number-average molecular weights ($M_n$) of 22000-42700 were successfully prepared (see Table 4 below):

TABLE 4

Characterization of Multi-Component PU Non-Cationomers Containing PCL-, PCL$_{POSS}$-, POSS-, and NMDEA-Units

| | | Molar ratio$^a$ | | | | $M_n$ | | Weight content (wt. %)$^d$ | | |
|---|---|---|---|---|---|---|---|---|---|---|
| Type | Sample | PCL | PCL$_{POSS}$ | POSS | NMDEA | (g · mol$^{-1}$)$^b$ | PDI$^c$ | PCL | POSS | NMDEA |
| 1 | 1a | 1.0 (1.0) | —$^e$ | 1.5 (0.8) | 2.0 (1.0) | 22000 | 1.2 | 70.8 | 16.6 | 2.2 |

TABLE 4-continued

Characterization of Multi-Component PU Non-Cationomers
Containing PCL-, PCL$_{POSS}$-, POSS-, and NMDEA-Units

| Type | Sample | Molar ratio[a] | | | | $M_n$ (g·mol$^{-1}$)[b] | PDI[c] | Weight content (wt. %)[d] | | |
|---|---|---|---|---|---|---|---|---|---|---|
| | | PCL | PCL$_{POSS}$ | POSS | NMDEA | | | PCL | POSS | NMDEA |
| | 1b | 0.5 (0.5) | 0.5 (0.4) | 0.75 (0.4) | 2.0 (1.1) | 26500 | 1.2 | 69.6[f] | 17.2[g] | 2.9 |
| | 1c | 0.5 (0.5) | 0.5 (0.3) | 1.5 (0.7) | 2.0 (1.2) | 22400 | 1.2 | 62.7[f] | 23.5[g] | 3.0 |
| | 1d | —[e] | 1.0 (1.0) | 1.5 (0.7) | 2.0 (1.3) | 27200 | 1.2 | 58.5[f] | 29.3[g] | 2.5 |
| 2 | 2a | 1.0 (1.0) | —[e] | 1.5 (1.2) | 2.0 (1.4) | 42700 | 1.2 | 64.9 | 20.1 | 2.9 |
| | 2b | —[e] | 1.0 (1.0) | 1.5 (0.7) | 2.0 (1.4) | 25100 | 1.2 | 62.3[f] | 26.1[g] | 2.6 |

[a]Molar ratios in the feed and the "actual" molar ratios of the obtained PU chains. The values in the parentheses are the actual molar ratios determined by $^1$H NMR.
[b,c]Number-average molecular weight (b) and polydispersity index (c) determined based on GPC.
[d]Determined based on $^1$H-NMR. The sum of weight contents of PCL, POSS, and NMDEA units is not 100% because that of HDI part is not included.
[e]Not used.
[f]The sum of weight contents of PCL unit and PCL part in the PCL$_{POSS}$ unit.
[g]The sum of weight contents of POSS part in the PCL$_{POSS}$ unit and POSS unit.

Example 12

Preparation of Aqueous Dispersions of PU Cationomers

Figure 26:
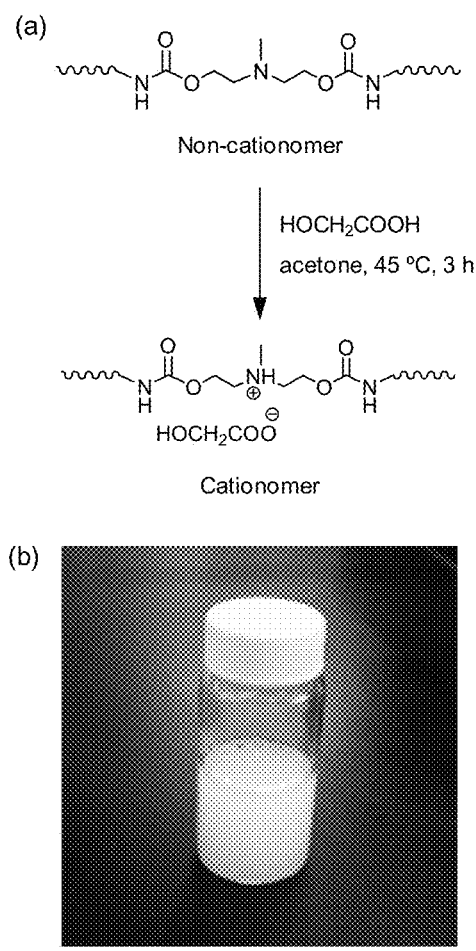
FIG. 26(a) is a schematic illustration showing quaternization reaction to prepare PCL-$PCL_{POSS1(or\ 2)}$-POSS1(or 2)-NMDEA PU cationomers, according to an embodiment of the present invention.
FIG. 26(b) is a photograph of an aqueous dispersion (1%, w/v) of the PU cationomer obtained through the acetone process, according to an embodiment of the present invention.

This Example describes the performance of a quaternization reaction for the tertiary amine units (NMDEA-units) of the PU's, described above, with glycolic acid in acetone to prepare PU cationomers (see FIG. 26a). After that, 1% (w/v) aqueous dispersions of the PU cationomers were prepared through the so-called acetone process. White opaque aqueous dispersions were obtained (see FIG. 26b).

In brief, a PU sample was dissolved in acetone to prepare 1% (w/v) solution in a 250 mL round-bottom flask. Then GA (1.0 equiv. of NMDEA unit) was added and dissolved. The reaction solution was stirred at 45° C. for 3 h for the quaternization reaction to form a PU cationomer. After that, pre-heated deionized water (similar volume with acetone) was added drop-wise with vigorous stirring at the temperature ranging from 45° C. to 55° C. (the temperature was gradually increased as deionized water was added). During the addition of water, the solution became translucent due to the formation of polymeric micelles. The PU dispersion in the acetone/water mixed solvent was then stirred at 70° C. until acetone was evaporated to form a 1% (w/v) aqueous, white opaque PU dispersion.

During this process, a portion of polymers (less than 20 wt. %) precipitated rather than remaining dispersed in water, which was removed. The 1% aqueous dispersions were condensed to 3% or 10% dispersions by rotovap at 45° C., and used to coat fibrous paper and human hair samples. For DSC measurements, the 10% aqueous dispersions were also casted onto a Teflon dish at 40-50° C. to make cast films, which were then dried under vacuum at room temperature for 2 days prior to the DSC measurements.

Example 13

This Example describes certain analysis that was carried out on the PU non-cationomers and cationomers.

Figure 19:
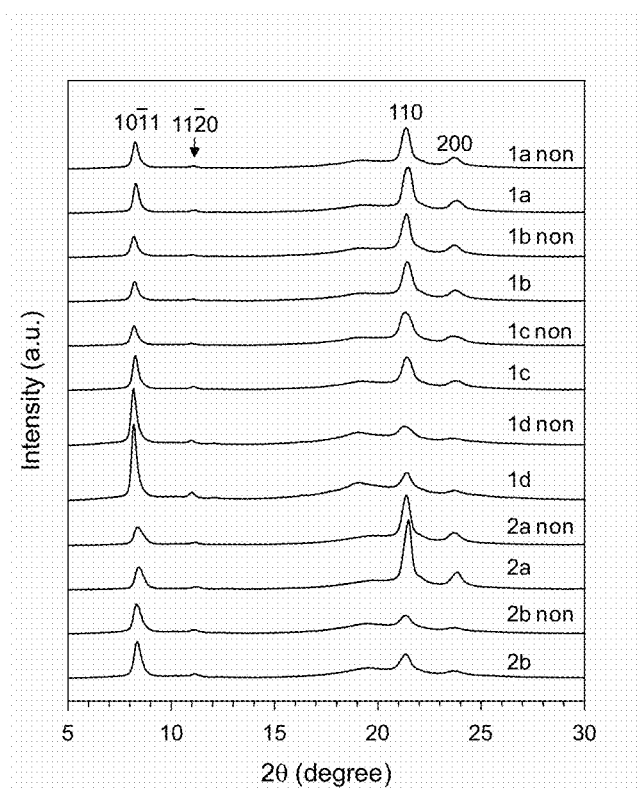
FIG. 19 is a graphical illustration showing WAXS profiles of non-cationomers ("non") and cationomers of samples 1a, 1b, 1c, 1d, 2a, and 2b; Miller indexes of POSS hexagonal crystals (10$\bar{1}$1 and 11$\bar{2}$0) and PCL orthorhombic crystals (110 and 200) are also show, according to an embodiment of the resent invention.

To study crystalline structure, wide-angle X-ray scattering (WAXS) was carried out for compression-molded films of the PU non-cationomers and cationomers (see FIG. 19). All of the samples showed diffraction peaks from both PCL and POSS phases. Depending on the weight contents of PCL and POSS phases, sequence structure of PU chains, and the types of POSS, the degrees of crystallinity ($X_c$) and apparent crystallite sizes (D) of the PU's were regulated (Table 5, below):

TABLE 5

Degree of Crystallinity ($X_c$) and Apparent Crystallite
Size (D) of PCL- and POSS-Phases of Multi-Component PU
Non-Cationomers and Cationomers[a]

| Sample | | $X_c$ (%)[b] | | D (nm)[c] | | |
|---|---|---|---|---|---|---|
| | | PCL | POSS | PCL 110 | PCL 200 | POSS 1011 |
| 1a | non-cationomer | 35 | 68 | 19 | 14 | 27 |
| | cationomer | 36 | 75 | 18 | 14 | 28 |
| 1b | non-cationomer | 37 | 70 | 19 | 14 | 25 |
| | cationomer | 39 | 66 | 17 | 12 | 26 |
| 1c | non-cationomer | 35 | 72 | 14 | 10 | 25 |
| | cationomer | 35 | 68 | 16 | 12 | 28 |
| 1d | non-cationomer | 20 | 69 | 12 | 8 | 29 |
| | cationomer | 18 | 70 | 16 | 14 | 30 |
| 2a | non-cationomer | 43 | 62 | 20 | 14 | 17 |
| | cationomer | 50 | 73 | 21 | 16 | 19 |
| 2b | non-cationomer | 24 | 65 | 15 | 11 | 20 |
| | cationomer | 34 | 67 | 15 | 10 | 22 |

[a]Compression-molded films were used.
[b]Determined by the curve deconvolution of WAXS profiles.
[c]Determined using the Scherrer equation, $D = \lambda/\beta \cdot \cos\theta$, where $\lambda$ is the X-ray wavelength (=0.15405 nm), $\beta$ is the full-width at half-maximum of each diffraction peak, and $\theta$ is the scattering angle.

Figure 20:
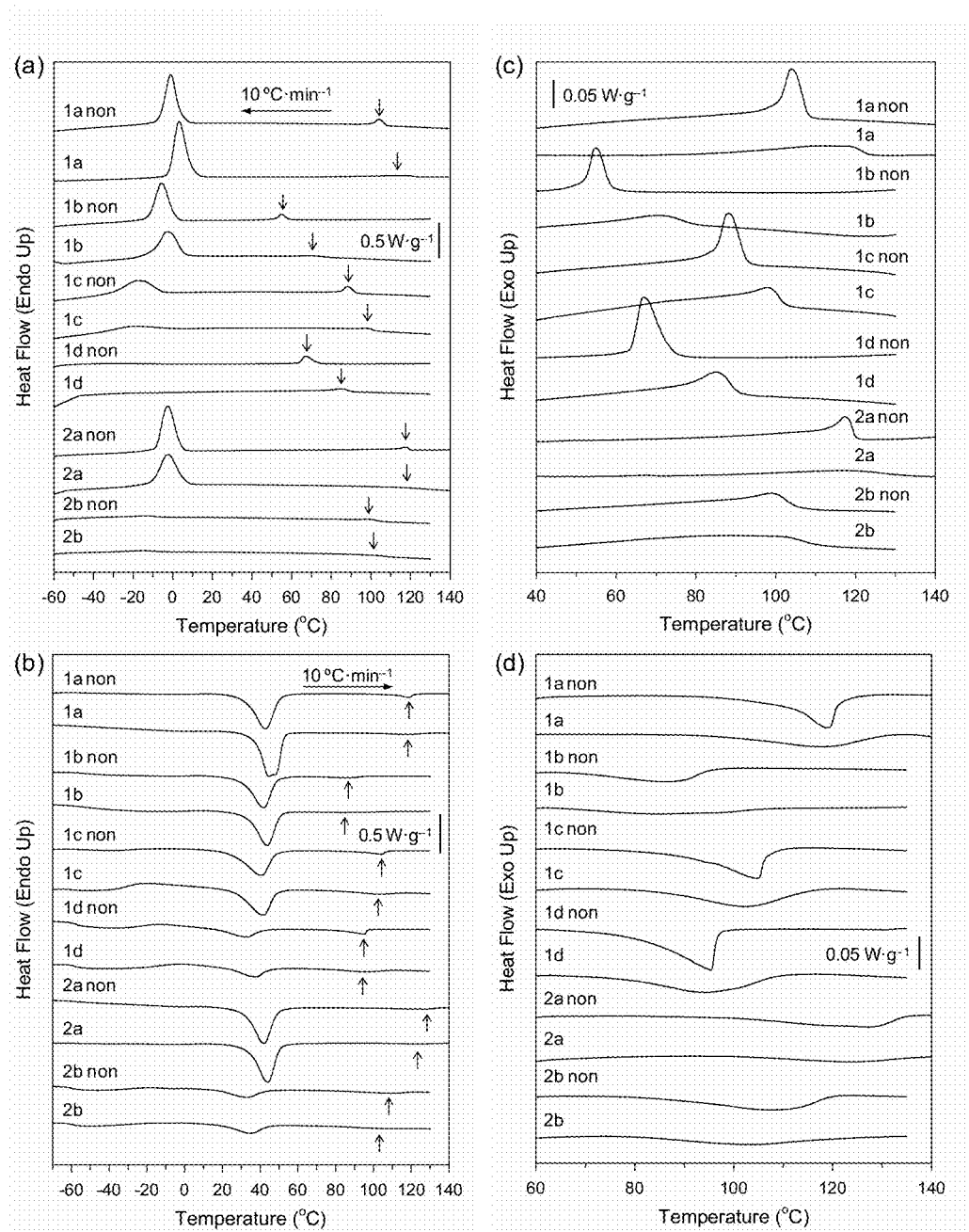
FIG. 20 is a graphical illustration, according to an embodiment of the present invention, showing DSC thermograms of non-cationomers ("non") and cationomers of samples 1a, 1b, 1c, 1d, 2a, and 2b during the cooling scan (a) and the 2nd heating scan (b). The arrows indicate the melt-crystallization peak ($T_{mc,POSS}$) and the melting peak ($T_{m,POSS}$) of POSS phase during the cooling scan and the 2nd heating scan, respectively. Enlarged views of (a) and (b) are shown in (c) and (d), respectively.

Thermal properties including crystallization and melting behavior were examined using differential scanning calorimetry (DSC, FIG. 20). The temperature and heat of melt-crystallization ($T_{mc}$ and $\Delta H_{mc}$) during the cooling scan (FIGS. 20a and 20c), those of cold-crystallization ($T_{cc}$ and $\Delta H_{cc}$) and melting ($T_m$ and $\Delta H_m$) during the 2nd heating scan (FIGS. 20b and 20d) are listed in Table 6 (below). The crystallization and melting behavior of especially POSS phase strongly depended on the weight contents of PCL and POSS phases, sequence structure of PU chains, and the presence of ionic groups along the PU chains.

TABLE 6

Thermal Properties[a] of PCL- and POSS-Containing Multi-Component PU Non-Cationomers and Cationomers

| Sample | | $T_{mc}$ (°C.)[b] | | $\Delta H_{mc}$ (J·g$^{-1}$)[c] | | $T_{cc}$ (°C.)[d] | $\Delta H_{cc}$ (J·g$^{-1}$)[e] | $T_m$ (°C.)[f] | | $\Delta H_m$ (J·g$^{-1}$)[g] | |
|---|---|---|---|---|---|---|---|---|---|---|---|
| | | PCL | POSS | PCL | POSS | PCL | PCL | PCL | POSS | PCL | POSS |
| 1a | non-cationomer | −1 | 104 | 31 | 2.8 | —[h] | 0 | 43 | 119 | 34 | 2.7 |
| | cationomer | 3 | 113 | 36 | 2.4 | —[h] | 0 | 44 | 118 | 40 | 2.4 |
| 1b | non-cationomer | −6 | 55 | 28 | 2.3 | —[h] | 0 | 42 | 87 | 31 | 1.9 |
| | cationomer | −3 | 70 | 26 | 1.4 | —[h] | 0 | 44 | 84 | 32 | 1.4 |
| 1c | non-cationomer | −18 | 88 | 21 | 3.0 | −11 | 4 | 41 | 105 | 29 | 3.1 |
| | cationomer | −20 | 98 | 14 | 2.7 | −21 | 13 | 42 | 103 | 29 | 2.8 |
| 1d | non-cationomer | — | 67 | 0 | 3.9 | −13 | 8 | 33 | 95 | 9 | 3.9 |
| | cationomer | — | 85 | 0 | 2.9 | −2 | 7 | 37 | 95 | 10 | 2.9 |
| 2a | non-cationomer | −3 | 117 | 32 | 1.3 | —[h] | 0 | 42 | 128 | 33 | 2.0 |
| | cationomer | −3 | 118 | 31 | 1.3 | —[h] | 0 | 44 | 123 | 34 | 1.0 |
| 2b | non-cationomer | −14 | 99 | 5 | 1.3 | −21 | 3 | 33 | 108 | 10 | 2.9 |
| | cationomer | −15 | 102 | 3 | 0.9 | −16 | 5 | 35 | 103 | 10 | 2.0 |

[a]Determined based on DSC runs (±10° C.·min$^{-1}$).
[b,c]Temperature (b) and heat (c) of melt-crystallization of PCL and POSS phases during the cooling run.
[d,e]Temperature (d) and heat (e) of cold-crystallization of PCL phase during the 2nd heating run.
[f,g]Temperature (f) and heat (g) of melting of PCL and POSS phases during the 2nd heating run.
[h]Not observed.

Figure 21:
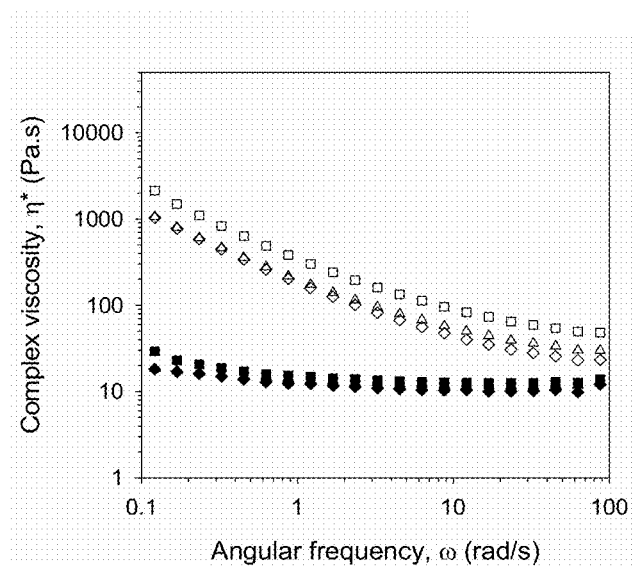
FIG. 21 is a graphical illustration showing angular frequency (ω)-dependence of complex viscosity (η*) of non-cationomers (solid symbols) and cationomers (open symbols) of sample 2a at 130° C. (square), 140° C. (triangle), and 150° C. (diamond), according to an embodiment of the resent invention.

Melt-rheology measurements of the PU non-cationomers and cationomers were performed to study the effect of presence of ionic groups in the PU chains. In the measurements of angular frequency (ω)-dependence of complex viscosity (η*) of a PU non-cationomer and cationomer at 130, 140, and 150° C. (FIG. 21), the PU non-cationomer showed almost constant η* in the whole ω range, the η* of the PU cationomer gradually decreased with an increase in ω value. This indicates the presence of thermally labile dynamic ionic aggregates in the PU cationomer.

Figure 22:
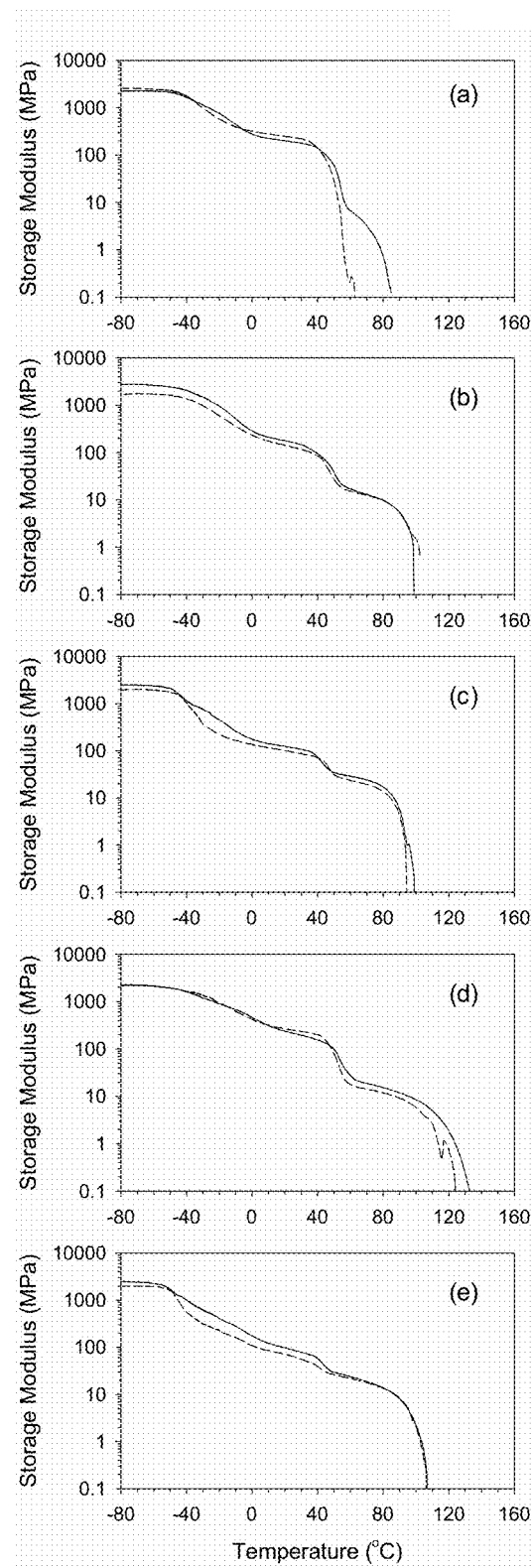
FIG. 22 is a graphical illustration showing storage modulus versus temperature during DMA measurements (1 Hz, 2° C.·min$^{-1}$) for non-cationomers (dashed lines) and cationomers (solid lines) of samples 1b (a), 1c (b), 1d (c), 2a (d), and 2b (e), according to an embodiment of the resent invention. The DMA measurement was not performed for both non-cationomer and cationomer of sample 1a due to the brittleness.

Thermo-mechanical properties of the PU non-cationomers and cationomers were examined using dynamic mechanical analysis (DMA), and the storage modulus (E') versus temperature curves are shown in FIG. 22. Almost all the samples exhibited three step decreases of E' values that are ascribable to the glass-rubber transition, melting of PCL phase, and melting of POSS phase, which corresponds to DSC data. It was found that the presence of ionic aggregates in the PU cationomer did not change the storage modulus values of the samples so much, compared to PU non-cationomers, and was helpful for stable physical cross-linking up to $T_{m,POSS}$.

Example 14

Figure 23:
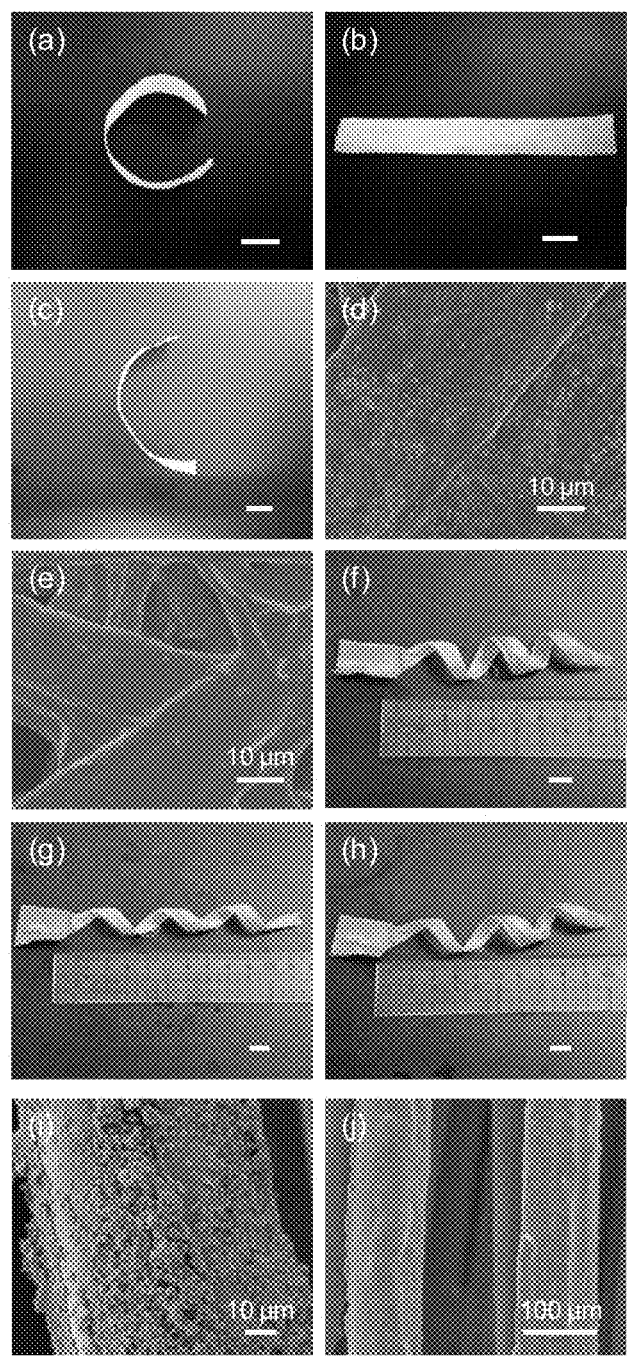
FIG. 23 shows SEM images of shape memory behavior and SEM images of sample 2a cationomer-coated fibrous paper strip (a-e) and sample 1b cationomer-coated hair tress (f-j): (a) a bended permanent shape; (b) a shape-fixed, straight temporary shape; (c) a recovered shape after heated at 80° C.; (d and e) SEM images of as-coated (d) and after melted the coating (e); (f) a curled permanent shape; (g) a deformed temporary shape after plastic deformation; (h) a recovered shape after heated at 60-65° C.; (i and j) SEM images of as-coated (i) and after melted the coating (j), according to an embodiment of the resent invention. The white scale bars in a, b, c, f, g, and h represent 10 mm.

Preparation of SMP-Coated Fibrous Paper and Shape Memory Experiment and Preparation of SMP-Coated Hairs and Shape Memory Experiment This Example describes the examination of shape memory behavior of a PU cationomer-coated fibrous paper (FIGS. 23a, 23b, and 23c) and another PU cationomer-coated human hair tress (FIGS. 23f, 23g, and 23h).

Regarding the examination of shape memory behavior of a PU cationomer-coated fibrous paper, a fibrous paper (Toyo Corporation, Tokyo, Japan) with a thickness of ~40 μm was used as a model substrate to study the shape memory behavior of thin SMP layer-coated flexible substrates. A rectangular strip (80 mm×12 mm; 16 mg) was cut from the fibrous paper sheet, and the both sides of the paper strip were coated with 3% (w/v) aqueous dispersion of sample 2a cationomer using a pipette. After dried under vacuum at room temperature for 2 days, the mass of the PU cationomer-coated paper strip was 36 mg. For the shape memory experiment, the PU cationomer-coated paper strip was set into a circle shape with the aid of a clip, heated at 135° C. for 10 min, and then cooled down to room temperature. This procedure provides a circle, permanent shape to it. After removing the clip, the PU cationomer-coated paper was heated at 80° C. for 10 min, deformed into a straight shape on a Teflon dish with the aid of weights, and cooled at 4° C. for 20 min to set a straight, temporary shape. After left it at room temperature for 30 min and then removing the weights, the PU cationomer-coated paper strip with the straight shape was heated at 80° C. for 10 min to see the shape recovery toward the circle shape. The shape recovery ratio was evaluated by measuring the curvature change.

Regarding the examination of shape memory behavior of a PU cationomer-coated human hair tress, a human hair tress (~500 hairs, length: 15 cm, diameter: 67±13 μm, provided by Procter & Gamble) was used as another model substrate to study the shape memory behavior of thin SMP layer-coated flexible substrates. Prior to the experiment, the hair tress was gently washed with shampoo (Pantene®) and repeatedly rinsed with deionized water to clean the surface of hairs and dried under vacuum at room temperature for a while. Then, the hair tress was set around a stick with rubber bands at both edges of the hair tress to form a curled shape. After that, 10% (w/v) aqueous dispersion of PU cationomer (sample 1b) was dropped onto the hair tress (3 wt. %) using a pipette. The PU-coated hair tress set around the stick with rubber bands was dried in the fume hood overnight and under vacuum at room temperature until complete. Then, the PU-coated hair tress with the stick and rubber bands was heated at 100° C. for 5 min to melt the PU cationomer and form a uniform coating layer, and cooled at 4° C. for 10 min and at room temperature for 30 min to set a curled permanent shape. The PU-coated hair tress with the curled shape was removed from the stick and hung vertically using a clamp and a stand (the length of the curled hair tress: $L_{permanent}$). Then a weight (~20 g) was clipped at the edge of the hair tress to deform the hairs, which was kept for 30 min at room temperature to set a deformed, temporary shape by plastic deformation of PU coating layer. After removing the weight, the deformed hair tress (length: $L_{deformed}$) was heated up to 60-65° C. for 3 min by gentle convective heating using a hair dryer, causing shape recovery (length: $L_{recovery}$). The shape recovery ratio ($R_r$) was calculated using the following equation:

$$R_r(\%) = (L_{deformed} - L_{recovery})/(L_{deformed} - L_{permanent}) \times 100$$

The results show that scanning electron microscopy (SEM) images of the "as-coated" PU-coated substrates and those after melting the coating layer for fibrous paper system (FIGS. 23d and 23e) and for human hair tress system (FIGS. 23i and 23j) indicate that the particle sizes of the waterborne PU cationomers were about 1 μm that is enough smaller than the substrates and that a uniform coating layer was formed on each of the substrates after melted. For both systems, curled deformed permanent shapes were set (FIGS. 23a and 23f) by deforming the PU-coated substrates, heating at $T > T_{m,POSS}$, and cooling to $T < T_{c,POSS}$ to program the POSS-based physical cross-linking structure. Then, temporary shapes were set for both systems by shape-fixing by deforming the PU-coated substrate at $T_{m,PCL} < T < T_{m,POSS}$ into a straight shape and cooling to $T < T_{c,PCL}$ with the external stress (FIG. 23b) or plastic deformation at room temperature (FIG. 23g). Those PU-coated substrates with temporary shapes were heated up at $T_{m,PCL} < T < T_{m,POSS}$ and showed shape recovery toward the original permanent shapes with good shape-recovery ratios about 75% (FIGS. 23c and 23h).

A waterborne shape memory polymer as disclosed herein can also be beneficially applied in the field of paper making to produce paper having shape memory. For example, in an embodiment a fibrous structure in the form of an absorbent paper, such as an absorbent tissue paper, can have a temporary three-dimensional structure formed during manufacture and/or converting, such that upon wetting, for example, the shape memory polymer causes the temporary structure to change shape into a different, beneficial, three-dimensional structure.

Therefore, in an embodiment, the invention can be described as a fibrous structure, which can be a paper product, and which further can be a tissue-towel product, in or on which is disposed a shape memory polymer. The shape memory polymer can be introduced in the "wet end" of a paper machine, such as in the furnish supplied to the headbox which then can become coated on fibers, or it can be added on by any known means such as spraying, extruding, or otherwise applying to a partially dewatered web anywhere along the paper machine or to a dry web in the "dry end" of a paper machine, or during converting, in which paper is converted into roll products, for example.

In general, fibrous structures of the present invention can have permanent three-dimensional structure, such as structure imparted by a papermaking belt during wet formation of a paper web comprising shape memory polymer, and three-dimensional structure imparted by a process of shaping a wet or dry shape memory polymer-treated paper during creping, calendaring, embossing or other web handling methods at appropriate temperatures and time. To form a temporary shape in a fibrous structure comprising shape memory polymer, the fibrous structure with permanent shape is subjected to further deformation, such as through nip embossing nip, press plates, or other deformation member that can strain the web, and hold in a strained configuration for appropriate time and temperature. The shape memory polymer-treated paper holds the temporary shape until wetted, after which time the temporary shape gives way to revert back to or towards the permanent three-dimensional shape.

Fibrous Structures

The fibrous structures of the present disclosure can be single-ply or multi-ply fibrous structures and can comprise cellulosic pulp fibers. Other naturally-occurring and/or non-naturally occurring fibers can also be present in the fibrous structures. In one example, the fibrous structures can be throughdried, or "through air dried (TAD)" as is known in the art. In one example, the fibrous structures can be wet-laid paper products. The fibrous structures can be incorporated into single- or multi-ply sanitary tissue products. The sanitary tissue products or fibrous structures can be in roll form where they are convolutedly wound or wrapped about themselves with or without the employment of a core. In other embodiments, the sanitary tissue products or fibrous structures can be in sheet form or can be at least partially folded over themselves.

Those of skill in the art will recognize that although this description illustrates various examples and forms of fibrous structures, sanitary tissue products, patterns, and papermaking belts of the present disclosure, those fibrous structures, sanitary tissue products, patterns, and papermaking belts are merely examples and are not intended to limit the present disclosure. It is believed that any absorbent paper product including sanitary tissue products including those made "conventionally" as is known in the art, can achieve the benefits and advantages of the paper products or sanitary tissue products of the present invention. The fibrous structures or sanitary tissue products of the present disclosure can apply to flat fibrous structures or sanitary tissue products, non-rolled fibrous structures or sanitary tissue products, folded fibrous structures or sanitary tissue products, and/or any other suitable formation for fibrous structures or sanitary tissue products.

The fibrous structures of the present invention can be made by using a patterned papermaking belt for forming three-dimensionally structured wet-laid webs as described in U.S. Pat. No. 4,637,859, issued Jan. 20, 1987, to Trokhan. Broadly, the papermaking belt of the present invention can include a reinforcing element (such as a woven belt) which can be thoroughly coated with a liquid photosensitive polymeric resin to a preselected thickness. A film or negative incorporating the pattern desired is juxtaposed on the liquid photosensitive resin. The resin is then exposed to light of an appropriate wave length through the film. This exposure to light causes curing of the resin in the exposed areas (i.e., white portions or non-printed portions in the film). Unexposed (and uncured) resin (under the black portions or printed portions in the film) is removed from the system leaving behind the cured resin forming the pattern desired, which pattern transfers during the wet-forming phase of papermaking to the fibrous structure.

In general, a method for making the fibrous structures of the present invention, the method can comprise the step of contacting an embryonic fibrous web with a molding member such that at least one portion of the embryonic fibrous web is deflected out-of-plane with respect to another portion of the embryonic fibrous web, which can form a permanent three-dimensional paper structure. The phrase "out-ofplane" as used herein means that the fibrous structure comprises a protuberance, such as a dome, or a cavity that extends away from the plane of the fibrous structure. The molding member can comprise a through-air-drying fabric having its filaments arranged to produce discrete elements within the fibrous structures of the present disclosure and/or the through-air-drying fabric or equivalent can comprise a resinous framework that defines continuous or substantially continuous deflection conduits or discrete deflection cells that allow portions of the fibrous structure to deflect into the conduits thus forming discrete elements (either relatively high or relatively low density depending on the molding member) within the fibrous structures of the present disclosure. In addition, a forming wire, such as a foraminous member can be used to receive a fibrous furnish and create an embryonic fibrous web thereon.

Further by way of example of a method for making fibrous structures of the present disclosure, the method can comprise the steps of:
(a) providing a fibrous furnish comprising fibers, the fibrous furnish optionally containing, in addition to water and cellulosic fibers, from about 0.1% to about 15%, or from about 0.1% to about 10%, or from about 0.25% to about 5% waterborne shape memory polymer, as described herein above; and
(b) depositing the fibrous furnish onto a molding member such that at least one fiber is deflected out-of-plane of the other fibers present on the molding member.

In still another example of a method for making a fibrous structure of the present disclosure, the method comprises the steps of:
(a) providing a fibrous furnish comprising fibers, the fibrous furnish optionally containing, in addition to water and cellulosic fibers, from about 0.1% to about 15%, or from about 0.1% to about 10%, or from about 0.25% to about 5% waterborne shape memory polymer, as described herein above;
(b) depositing the fibrous furnish onto a foraminous member to form an embryonic fibrous web;
(c) associating the embryonic fibrous web with a molding member such that at least one fiber is deflected out-of-plane of the other fibers present in the embryonic fibrous web; and
(d) drying said embryonic fibrous web such that that a three-dimensional, dried fibrous structure is formed.

In another example of a method for making the fibrous structures of the present disclosure, the method can comprise the steps of:
(a) providing a fibrous furnish comprising fibers, the fibrous furnish optionally containing, in addition to water and cellulosic fibers, from about 0.1% to about 15%, or from about 0.11% to about 10%, or from about 0.25% to about 5% waterborne shape memory polymer, as described herein above;
(b) depositing the fibrous furnish onto a foraminous member such that an embryonic fibrous web is formed;
(c) associating the embryonic web with a molding member comprising discrete deflection cells or substantially continuous deflection conduits;
(d) deflecting the fibers in the embryonic fibrous web into the discrete deflection cells or substantially continuous deflection conduit and removing water from the embryonic web through the discrete deflection cells or substantially continuous deflection conduit so as to form an intermediate fibrous web under such conditions that the deflection of fibers is initiated no later than the time at which the water removal through the discrete deflection cells or the substantially continuous deflection conduits is initiated;
(e) optionally, drying the intermediate fibrous web; and
(f) optionally, foreshortening the intermediate fibrous web.

Figure 27:
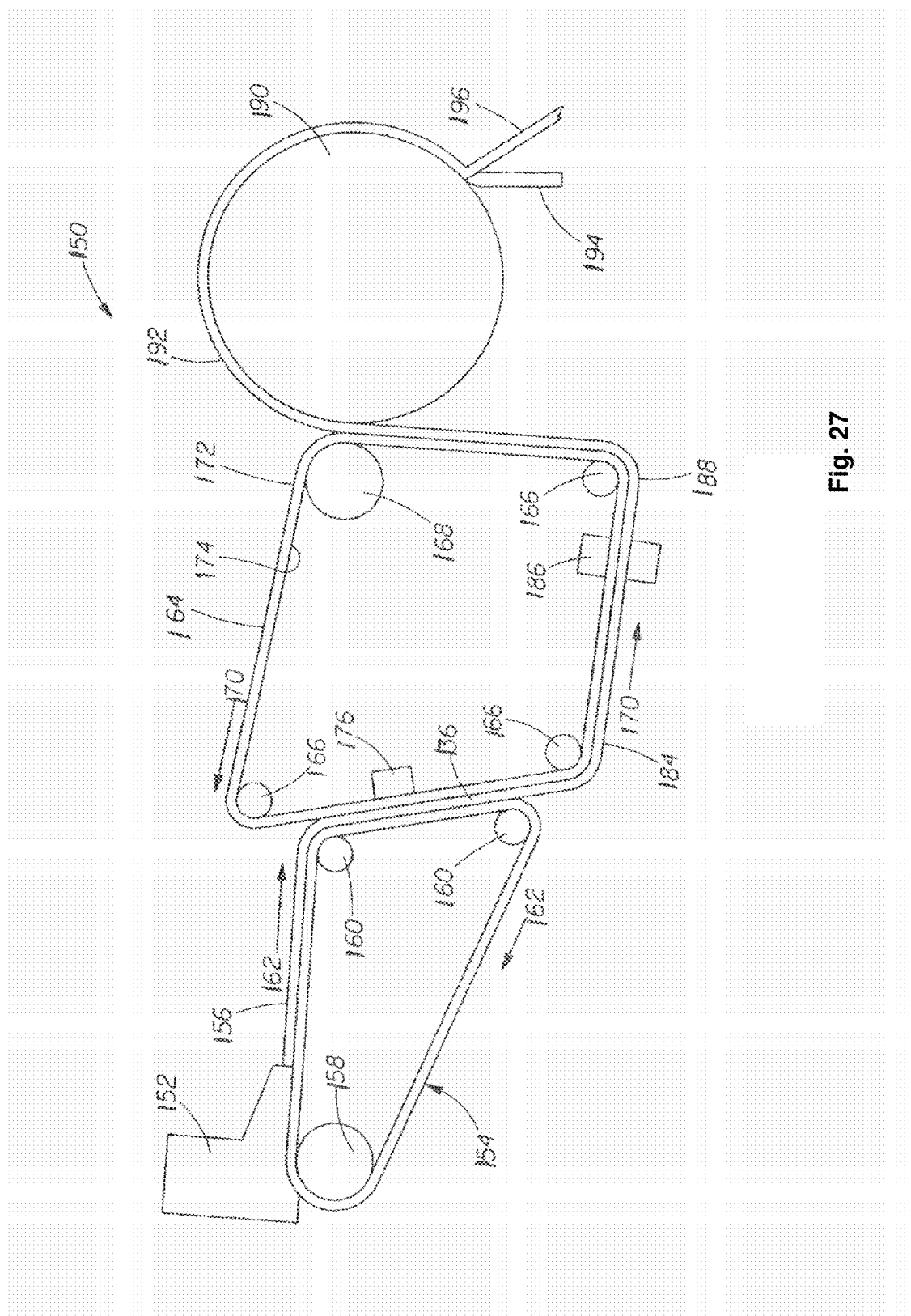
FIG. 27 is a schematic representation of a process and apparatus for making a fibrous structure, including an absorbent paper product.

FIG. 27 is a simplified, schematic representation of one example of a continuous fibrous structure making process and machine useful in the practice of the present disclosure.

As shown in FIG. 27, one example of a process and equipment, represented as 150, for making fibrous structures according to the present disclosure comprises supplying an aqueous dispersion of fibers (a fibrous furnish) to a headbox 152 which can be of any design known to those of skill in the art. From the headbox 152, the aqueous dispersion of fibers can be delivered to a foraminous member 154, which can be a Fourdrinier wire, to produce an embryonic fibrous web 156. In an embodiment, in addition to water and cellulosic fibers, the furnish delivered from the headbox can comprise from about 0.1% to about 15%, or from about 0.1% to about 10%, or from about 0.25% to about 5% waterborne shape memory polymer, as described herein above. The waterborne shape memory polymer can thus be dispersed generally evenly upon the constituent fibers of the resulting paper web, remaining on the fibers through the drying and, optionally, the converting process.

The foraminous member 154 can be supported by a breast roll 158 and a plurality of return rolls 160 of which only two are illustrated. The foraminous member 154 can be propelled in the direction indicated by directional arrow 162 by a drive means, not illustrated. Optional auxiliary units and/or devices commonly associated with fibrous structure making machines and with the foraminous member 154, but not illustrated, comprise forming boards, hydrofoils, vacuum boxes, tension rolls, support rolls, wire cleaning showers, and other various components known to those of skill in the art.

After the aqueous dispersion of fibers is deposited onto the foraminous member 154, the embryonic fibrous web 156 is formed, typically by the removal of a portion of the aqueous dispersing medium by techniques known to those skilled in the art, with at least a portion of the waterborne shape memory polymer component of the furnish remaining as a deposit or coating on the fibers deposited on the foraminous member. Vacuum boxes, forming boards, hydrofoils, and other various equipment known to those of skill in the art are useful in effectuating water removal. The embryonic fibrous web 156 can travel with the foraminous member 154 about return roll 160 and can be brought into contact with a molding member 164, also referred to as a paper-making belt. While in contact with the molding member 164, the embryonic fibrous web 156 can be deflected, rearranged, and/or further dewatered.

The molding member 164 can be in the form of an endless belt. In this simplified representation, the molding member 164 passes around and about molding member return rolls 166 and impression nip roll 168 and can travel in the direction indicated by directional arrow 170. Associated with the molding member 164, but not illustrated, can be various support rolls, other return rolls, cleaning means, drive means, and other various equipment known to those of skill in the art that may be commonly used in fibrous structure making machines.

Regardless of the physical form which the molding member 164 takes, whether it is an endless belt as just discussed or some other embodiment, such as a stationary plate for use in making handsheets or a rotating drum for use with other types of continuous processes, it can have certain physical characteristics. First, the molding member 164 can be foraminous. That is to say, it may possess continuous passages connecting its first surface 172 (or "upper surface" or "working surface"; i.e., the surface with which the embryonic fibrous web 156 is associated) with its second surface 174 (or "lower surface; i.e., the surface with which the molding member return rolls 166 are associated). In other words, the molding member 164 can be constructed in such a manner that when water is caused to be removed from the embryonic fibrous web 156, as by the application of differential fluid pressure, such as by a vacuum box 176, and when the water is removed from the embryonic fibrous web 156 in the direction of the molding member 164, the water can be discharged from the system without having to again contact the embryonic fibrous web 156 in either the liquid or the vapor state.

Second, the first surface 172 of the molding member 164 can comprise one or more discrete raised portions 14 or one or more continuous or substantially continuous members. The discrete raised portions 14 or the continuous substantially continuous members can be made using any suitable material. For example, a resin, such as a photocurable resin, for example, can be used to create the discrete raised portions 14 or the continuous or substantially continuous member. The discrete raised portions 14 or the continuous or substantially continuous member can be arranged to produce the fibrous structures of the present disclosure when utilized in a suitable fibrous structure making process.

In one example, the molding member 164 can be an endless belt which can be constructed by, among other methods, a method adapted from techniques used to make stencil screens. By "adapted" it is meant that the broad, overall techniques of making stencil screens are used, but improvements, refinements, and modifications as discussed below are used to make the molding member 164 having significantly greater thickness than the usual stencil screen.

Broadly, a reinforcing element 202 or (such as a woven belt) is thoroughly coated with a liquid photosensitive polymeric resin to a preselected thickness. A film or negative incorporating the pattern is juxtaposed on the liquid photosensitive resin. The resin is then exposed to light of an appropriate wave length through the film. This exposure to light causes curing of the resin in the exposed areas (i.e., white portions or non-printed portions in the film). Uncured resin (under the black portions or printed portions in the film) is removed from the system leaving behind the cured resin forming the pattern illustrated herein.

Suitable photosensitive resins can be readily selected from the many available commercially. They are typically materials, usually polymers, which cure or cross-link under the influence of activating radiation, usually ultraviolet (UV) light. References containing more information about liquid photosensitive resins include Green et al., "Photocrosslinkable Resin Systems," J. Macro. Sci-Revs. Macro. Chem., C21(2), 187-273 (1981-82); Boyer, "A Review of Ultraviolet Curing Technology," Tappi Paper Synthetics Conf. Proc., Sep. 25-27, 1978, pp 167-172; and Schmidle, "Ultraviolet Curable Flexible Coatings," J. of Coated Fabrics, 8, 10-20 (July, 1978). In one example, the discrete raised portions 14, 206 or the continuous or substantially continuous members 206' are made from the Merigraph series of resins made by Hercules Incorporated of Wilmington, Del.

The molding members of the present disclosure can be made, or partially made, according to the process described in U.S. Pat. No. 4,637,859, issued Jan. 20, 1987, to Trokhan.

After the embryonic fibrous web 156 has been associated with the molding members 164, fibers within the embryonic fibrous web 156 are deflected into the continuous or substantially continuous deflection conduits 16 present in the molding members 164. In one example of this process step, there is essentially no water removal from the embryonic fibrous web 156 through the continuous or substantially continuous deflection conduits 16 after the embryonic fibrous web 156 has been associated with the molding members 164 but prior to the deflecting of the fibers into the continuous or substantially continuous deflection conduits 16 to form a three-dimensional paper web. Further water removal from the embryonic fibrous web 156 can occur during and/or after the time the fibers are being deflected into the continuous or substantially continuous deflection conduits 16. Water removal from the embryonic fibrous web 156 can continue until the consistency of the embryonic fibrous web 156 associated with the molding member 164 is increased to from about 20% to about 35%. Once this consistency of the embryonic fibrous web 156 is achieved, then the embryonic fibrous web 156 is referred to as an intermediate fibrous web 184. During the process of forming the embryonic fibrous web 156, sufficient water can be removed, such as by a noncompressive process, from the embryonic fibrous web 156 before it becomes associated with the molding member 164 so that the consistency of the embryonic fibrous web 156 can be from about 10% to about 30%.

As noted, water removal occurs both during and after deflection; this water removal can result in a decrease in fiber mobility in the embryonic fibrous web. This decrease in fiber mobility may tend to fix and/or freeze the fibers in place after they have been deflected and rearranged. Of course, the drying of the web in a later step in the process of this disclosure serves to more firmly fix and/or freeze the fibers in a generally three-dimensional configuration, with the third dimension being generally the "Z-direction" orthogonal to the plane of the paper web, as is understood in the art.

Any convenient methods conventionally known in the papermaking art can be used to dry the intermediate fibrous web 184. Examples of such suitable drying process include subjecting the intermediate fibrous web 184 to conventional and/or flow-through dryers and/or Yankee dryers.

In one example of a drying process, the intermediate fibrous web 184 in association with the molding member 164 passes around the molding member return roll 166 and travels in the direction indicated by directional arrow 170. The intermediate fibrous web 184 can first pass through an optional predryer 186. This predryer 186 can be a conventional flow-through dryer (hot air dryer) known to those skilled in the art. Optionally, the predryer 186 can be a so-called capillary dewatering apparatus. In such an apparatus, the intermediate fibrous web 184 passes over a sector of a cylinder having preferential-capillary-size pores through its cylindrical-shaped porous cover. Optionally, the predryer 186 can be a combination capillary dewatering apparatus and flow-through dryer. The quantity of water removed in the predryer 186 can be controlled so that a predried fibrous web 188 exiting the predryer 186 has a consistency of from about 30% to about 98%. The predried fibrous web 188, which can still be associated with papermaking belt 200, can pass around another papermaking belt return roll 166 and as it travels to an impression nip roll 168. As the predried fibrous web 188 passes through the nip formed between impression nip roll 168 and a surface of a Yankee dryer 190, the pattern formed by the top surface 172 of the molding member 164 is impressed into the predried fibrous web 188 to form discrete elements (relatively high density) or, alternatively, a substantially continuous network (relatively high density) imprinted in the fibrous web 192. The imprinted fibrous web 192 can then be adhered to the surface of the Yankee dryer 190 where it can be dried to a consistency of at least about 95%.

The imprinted fibrous web 192 can then be foreshortened by creping the web 192 with a creping blade 194 to remove the web 192 from the surface of the Yankee dryer 190 resulting in the production of a creped fibrous structure 196 in accordance with the present disclosure. As used herein, foreshortening refers to the reduction in length of a dry (having a consistency of at least about 90% and/or at least about 95%) fibrous web which occurs when energy is applied to the dry fibrous web in such a way that the length of the fibrous web is reduced and the fibers in the fibrous web are rearranged with an accompanying disruption of fiber-fiber bonds. Foreshortening can be accomplished in any of several ways. One common method of foreshortening is creping. The creped fibrous structure 196 can be subjected to post processing steps such as calendaring, tuft generating operations, embossing, and/or converting.

In addition to the Yankee fibrous structure making process/method, the fibrous structures of the present disclosure can be made using a Yankeeless fibrous structure making process/method. Such a process oftentimes utilizes transfer fabrics to permit rush transfer of the embryonic fibrous web prior to drying. The fibrous structures produced by such a Yankeeless fibrous structure making process oftentimes a substantially uniform density.

The molding member/papermaking belts of the present disclosure can be utilized to imprint discrete elements and a substantially continuous network into a fibrous structure during a through-air-drying operation.

However, such molding members/papermaking belts can also be utilized as forming members or foraminous members upon which a fiber slurry is deposited.

As discussed above, the fibrous structure can be embossed during a converting operation to produce the fibrous structures of the present disclosure. For example, the discrete elements and/or the continuous or substantially continuous network can be imparted to a fibrous structure by embossing. Additionally, waterborne shape memory polymer can be added to the dry paper web during the converting operation, such as before, during, or after an embossing step. For example, waterborne shape memory polymer can be sprayed, such as by a relatively uniform spray nozzle arrangement across the width of the paper web, or otherwise applied by means known in the art for applying liquid substances to a moving web structure, at a level desired, such as from about 0.1% to about 15% by weight of dry fiber, or from about 0.1% to about 10% by weight of dry fiber, or from about 0.25% to about 5% by weight of dry fiber.

To form a temporary shape in a fibrous structure comprising shape memory polymer, the fibrous structure is subjected to deformation, such as through nip embossing nip, press plates, or other deformation member that can strain the web, and hold in a strained configuration for from about 0.01 secs to about 1 mins at a temperature of from about 20 degrees C. to about 100 degrees C., with the time and temperature selection being made according to the basis weight of the paper, the amount of shape memory polymer, and the degree of strain, all of which can be determined without undue experimentation.

In an embodiment, a fibrous structure of cellulosic fibers formed on a forming structure as described. A two-ply fibrous structure was made in the laboratory using a rubber-to-steel embossing plate. The embossing plate was approximately 6"×6", with a pattern of raised knobs. There were about 420 knobs on the steel plate and they covered about 10% of the total plate area. One ply of paper, also about 6"×6", was placed over the emboss plate. The 1-ply paper basis weight was about 25-26 g/m$^2$. Shape memory polymer was applied to the paper using a 1 ml syringe with a 0.013 ID tip. The polymer was delivered in a 5% by weight, aqueous suspension. The polymer was only applied to the paper regions corresponding to the emboss pattern. The polymer was metered from the syringe to achieve the desired addition level, in this case about 5% by weight (dry polymer/dry 2-ply paper) in the area of application. For additional level calculations, it was assumed the polymer would spread to cover about 30% of the paper sample. The second ply of paper was placed on top of the first immediately after polymer application, covered with a Shore 60A rubber sheet and pressed for about 30 seconds under a load of about 1600 lbf. After removal from the press, the sample was air dried while still on the emboss plate. This process formed the permanent polymer shape. The sample can then be subject to various tensile or compression strains at a temperature of about 80° C. for a time of up to about 2 minutes to set the temporary shape, from which it will recover upon wetting.

The present invention contemplates the use of a variety of paper making fibers, such as, natural fibers, synthetic fibers, as well as any other suitable fibers, starches, and combinations thereof. Paper making fibers useful in the present invention include cellulosic fibers commonly known as wood pulp fibers. Applicable wood pulps include chemical pulps, such as Kraft, sulfite and sulfate pulps, as well as mechanical pulps including, groundwood, thermomechanical pulp, chemically modified, and the like. Chemical pulps may be used in tissue towel embodiments since they are known to those of skill in the art to impart a superior tactical sense of softness to tissue sheets made therefrom. Pulps derived from deciduous trees (hardwood) and/or coniferous trees (softwood) can be utilized herein. Such hardwood and softwood fibers can be blended or deposited in layers to provide a stratified web. Exemplary layering embodiments and processes of layering are disclosed in U.S. Pat. Nos. 3,994,771 and 4,300,981. Additionally, other natural fibers such as cotton linters, bagesse, and the like, can be used. Additionally, fibers derived from recycled paper, which may contain any of all of the categories as well as other non-fibrous materials such as fillers and adhesives used to manufacture the original paper product may be used in the present web. In addition, fibers and/or filaments made from polymers, specifically hydroxyl polymers, may be used in the present invention. Non-limiting examples of suitable hydroxyl polymers include polyvinyl alcohol, starch, starch derivatives, chitosan, chitosan derivatives, cellulose derivatives, gums, arabinans, galactans, and combinations thereof. Additionally, other synthetic fibers such as rayon, polyethylene, and polypropylene fibers can be used within the scope of the present invention. Further, such fibers may be latex bonded.

In one embodiment the paper can be produced by forming a predominantly aqueous slurry comprising about 95% to about 99.9% water. In one embodiment the non-aqueous component of the slurry used to make the fibrous structure can comprise from about 5% to about 80% of eucalpyptus fibers by weight of the non-aqueous components of the slurry. In another embodiment the non-aqueous components can comprise from about 8% to about 60% of eucalpyptus fibers by weight of the non aqueous components of the slurry, and in yet another embodiment from about 15% to about 30% of eucalyptus fibers by weight of the non-aqueous component of the slurry. In one embodiment the slurry can comprise of about 45% to about 60% of Northern Softwood Kraft fibers with up to 20% Southern Softwood Kraft co-refined together, about 25% to about 35% unrefined Eucalyptus fibers and from about 5% to about 30% of either repulped product broke or thermo-mechanical pulp. The aqueous slurry can be pumped to the headbox of the papermaking process.

In one embodiment the present invention may comprise a co-formed fibrous structure. A co-formed fibrous structure comprises a mixture of at least two different materials wherein at least one of the materials comprises a non-naturally occurring fiber, such as a polypropylene fiber, and at least one other material, different from the first material, comprising a solid additive, such as another fiber and/or a particulate. In one example, a co-formed fibrous structure comprises solid additives, such as naturally occurring fibers, such as wood pulp fibers, and non-naturally occurring fibers, such as polypropylene fibers.

Synthetic fibers useful herein include any material, such as, but not limited to polymers, those selected from the group consisting of polyesters, polypropylenes, polyethylenes, polyethers, polyamides, polyhydroxyalkanoates, polysaccharides, and combinations thereof. More specifically, the material of the polymer segment may be selected from the group consisting of poly(ethylene terephthalate), poly(butylene terephthalate), poly(1,4-cyclohexylenedimethylene terephthalate), isophthalic acid copolymers (e.g., terephthalate cyclohexylenedimethylene isophthalate copolymer), ethylene glycol copolymers (e.g., ethylene terephthalate cyclohexylenedimethylene copolymer), polycaprolactone, poly(hydroxyl ether ester), poly(hydroxyl ether amide), polyesteramide, poly(lactic acid), polyhydroxybutyrate, and combinations thereof.

Further, the synthetic fibers can be a single component (i.e., single synthetic material or a mixture to make up the entire fiber), bi-component (i.e., the fiber is divided into regions, the regions including two or more different synthetic materials or mixtures thereof and may include co-extruded fibers) and combinations thereof. It is also possible to use bicomponent fibers, or simply bicomponent or sheath polymers. Nonlimiting examples of suitable bicomponent fibers are fibers made of copolymers of polyester (polyethylene terephthalate)/polyester (polyethylene terephthalate) otherwise known as "CoPET/PET" fibers, which are commercially available from Fiber Innovation Technology, Inc., Johnson City, Tenn.

These bicomponent fibers can be used as a component fiber of the structure, and/or they may be present to act as a binder for the other fibers present. Any or all of the synthetic fibers may be treated before, during, or after the process of the present invention to change any desired properties of the fibers. For example, in certain embodiments, it may be desirable to treat the synthetic fibers before or during the papermaking process to make them more hydrophilic, more wettable, etc.

These multicomponent and/or synthetic fibers are further described in U.S. Pat. No. 6,746,766, issued on Jun. 8, 2004; U.S. Pat. No. 6,946,506, issued Sep. 20, 2005; U.S. Pat. No. 6,890,872, issued May 10, 2005; US Publication No. 2003/0077444A1, published on Apr. 24, 2003; US Publication No. 2003/0168912A1, published on Nov. 14, 2002; US Publication No. 2003/0092343A1, published on May 15, 2003; US Publication No. 2002/0168518A1, published on Nov. 14, 2002; US Publication No. 2005/0079785A1, published on Apr. 14, 2005; US Publication No. 2005/0026529A1, published on Feb. 3, 2005; US Publication No. 2004/0154768A1, published on Aug. 12, 2004; US Publication No. 2004/0154767, published on Aug. 12, 2004; US Publication No. 2004/0154769A1, published on Aug. 12, 2004; US Publication No. 2004/0157524A1, published on Aug. 12, 2004; US Publication No. 2005/0201965A1, published on Sep. 15, 2005.

A manufacturing process for making a fibrous structure of the present invention may comprise any processes and apparatus known for the manufacture of tissue-towel paper product. Embodiments of these processes and apparatus may be made according to the teachings of U.S. Pat. No. 4,191,609 issued Mar. 4, 1980 to Trokhan; U.S. Pat. No. 4,300,981 issued to Carstens on Nov. 17, 1981; U.S. Pat. No. 4,191,609 issued to Trokhan on Mar. 4, 1980; U.S. Pat. No. 4,514,345 issued to Johnson et al. on Apr. 30, 1985; U.S. Pat. No. 4,528,239 issued to Trokhan on Jul. 9, 1985; U.S. Pat. No. 4,529,480 issued to Trokhan on Jul. 16, 1985; U.S. Pat. No. 4,637,859 issued to Trokhan on Jan. 20, 1987; U.S. Pat. No. 5,245,025 issued to Trokhan et al. on Sep. 14, 1993; U.S. Pat. No. 5,275,700 issued to Trokhan on Jan. 4, 1994; U.S. Pat. No. 5,328,565 issued to Rasch et al. on Jul. 12, 1994; U.S. Pat. No. 5,334,289 issued to Trokhan et al. on Aug. 2, 1994; U.S. Pat. No. 5,364,504 issued to Smurkowski et al. on Nov. 15, 1995; U.S. Pat. No. 5,527,428 issued to Trokhan et al. on Jun. 18, 1996; U.S. Pat. No. 5,556,509 issued to Trokhan et al. on Sep. 17, 1996; U.S. Pat. No. 5,628,876 issued to Ayers et al. on May 13, 1997; U.S. Pat. No. 5,629,052 issued to Trokhan et al. on May 13, 1997; U.S. Pat. No. 5,637,194 issued to Ampulski et al. on Jun. 10, 1997; U.S. Pat. No. 5,411,636 issued to Hermans et al. on May 2, 1995; EP 677612 published in the name of Wendt et al. on Oct. 18, 1995, and U.S. Patent Application 2004/0192136A1 published in the name of Gusky et al. on Sep. 30, 2004.

The tissue-towel substrates may be manufactured via a wet-laid making process where the resulting web is through-air-dried or conventionally dried. Optionally, the substrate may be foreshortened by creping or by wet microcontraction. Creping and/or wet microcontraction are disclosed in commonly assigned U.S. Pat. No. 6,048,938 issued to Neal et al. on Apr. 11, 2000; U.S. Pat. No. 5,942,085 issued to Neal et al. on Aug. 24, 1999; U.S. Pat. No. 5,865,950 issued to Vinson et al. on Feb. 2, 1999; U.S. Pat. No. 4,440,597 issued to Wells et al. on Apr. 3, 1984; U.S. Pat. No. 4,191,756 issued to Sawdai on May 4, 1980; and U.S. Pat. No. 6,187,138 issued to Neal et al. on Feb. 13, 2001.

Uncreped tissue paper, in one embodiment, refers to tissue paper which is non-compressively dried, by through air drying. Resultant through air dried webs are pattern densified such that zones of relatively high density are dispersed within a high bulk field, including pattern densified tissue wherein zones of relatively high density are continuous and the high bulk field is discrete. The techniques to produce uncreped tissue in this manner are taught in the prior art. For example, Wendt, et. al. in European Patent Application 0 677 612A2, published Oct. 18, 1995; Hyland, et. al. in European Patent Application 0 617 164 A1, published Sep. 28, 1994; and Farrington, et. al. in U.S. Pat. No. 5,656,132 published Aug. 12, 1997.

Other materials are also intended to be within the scope of the present invention as long as they do not interfere or counteract any advantage presented by the instant invention.

The fibrous structure product according to the present invention can have domes, as taught by commonly assigned U.S. Pat. No. 4,528,239 issued Jul. 9, 1985 to Trokhan; U.S. Pat. No. 4,529,480 issued Jul. 16, 1985 to Trokhan; U.S. Pat.

No. 5,275,700 issued Jan. 4, 1994 to Trokhan; U.S. Pat. No. 5,364,504 issued Nov. 15, 1985 to Smurkoski et al.; U.S. Pat. No. 5,527,428 issued Jun. 18, 1996 to Trokhan et al.; U.S. Pat. No. 5,609,725 issued Mar. 11, 1997 to Van Phan; U.S. Pat. No. 5,679,222 issued Oct. 21, 1997 to Rasch et al.; U.S. Pat. No. 5,709,775 issued Jan. 20, 1995 to Trokhan et al.; U.S. Pat. No. 5,795,440 issued Aug. 18, 1998 to Ampulski et al.; U.S. Pat. No. 5,900,122 issued May 4, 1999 to Huston; U.S. Pat. No. 5,906,710 issued May 25, 1999 to Trokhan; U.S. Pat. No. 5,935,381 issued Aug. 10, 1999 to Trokhan et al.; and U.S. Pat. No. 5,938,893 issued Aug. 17, 1999 to Trokhan et al.

In one embodiment the plies of the multi-ply fibrous structure may be the same substrate respectively or the plies may comprise different substrates combined to create desired consumer benefits. In one embodiment the fibrous structures comprise two plies of tissue substrate. In another embodiment the fibrous structure comprises a first ply, a second ply, and at least one inner ply.

In one embodiment of the present invention, the fibrous structure product has a plurality of embossments. In one embodiment the embossment pattern is applied only to the first ply, and therefore, each of the two plies serve different objectives and are visually distinguishable. For instance, the embossment pattern on the first ply provides, among other things, improved aesthetics regarding thickness and quilted appearance, while the second ply, being unembossed, is devised to enhance functional qualities such as absorbency, thickness and strength. In another embodiment the fibrous structure product is a two ply product wherein both plies comprise a plurality of embossments.

Suitable means of embossing include those disclosed in U.S. Pat. No. 3,323,983 issued to Palmer on Sep. 8, 1964; U.S. Pat. No. 5,468,323 issued to McNeil on Nov. 21, 1995; U.S. Pat. No. 5,693,406 issued to Wegele et al. on Dec. 2, 1997; U.S. Pat. No. 5,972,466 issued to Trokhan on Oct. 26, 1999; U.S. Pat. No. 6,030,690 issued to McNeil et al. on Feb. 29, 2000; and U.S. Pat. No. 6,086,715 issued to McNeil on July 11.

Suitable means of laminating the plies include but are not limited to those methods disclosed in commonly assigned U.S. Pat. No. 6,113,723 issued to McNeil et al. on Sep. 5, 2000; U.S. Pat. No. 6,086,715 issued to McNeil on Jul. 11, 2000; U.S. Pat. No. 5,972,466 issued to Trokhan on Oct. 26, 1999; U.S. Pat. No. 5,858,554 issued to Neal et al. on Jan. 12, 1999; U.S. Pat. No. 5,693,406 issued to Wegele et al. on Dec. 2, 1997; U.S. Pat. No. 5,468,323 issued to McNeil on Nov. 21, 1995; U.S. Pat. No. 5,294,475 issued to McNeil on Mar. 15, 1994.

Waterborne shape memory polymers can be added to a paper product either during papermaking, such as being introduced in the head box in the fiber slurry, or during the converting stage, which can include application by any of known spraying, extruding, or other coating steps before, during, or after the step of embossing and/or laminating.

While several embodiments of the invention have been discussed, it will be appreciated by those skilled in the art that various modifications and variations of the present invention are possible. Such modifications do not depart from the spirit and scope of the present invention.

What is claimed is:

1. A waterborne shape memory polymer comprising structural units repeating along a backbone in a linear sequence, wherein each structural unit comprises:
   a switching segment comprising PCL diol;
   a chargeable unit comprising N-methyldiethanolamine (NMDEA);
   a cross-linkable unit comprising POSS diol, wherein said cross-linkable unit connects said switchable segment to said chargeable unit to form a single polymer chain, wherein:

the cross-linkable unit is positioned between the switching segment and the chargeable unit through an amido linkage of a difunctional amido monomer of the switching segment along the backbone in the linear sequence, indirectly connecting the switching segment and the chargeable unit, and the waterborne shape memory polymer is dispersible in water; and 1,6-hexanediisocyanate (HDI); and wherein the waterborne shape memory polymer has the following structure:

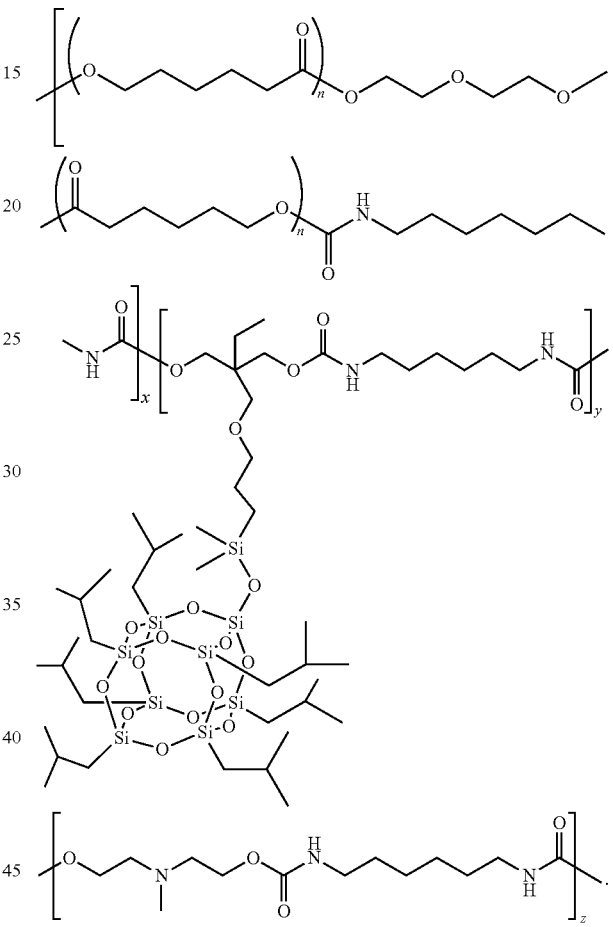

2. The waterborne shape memory polymer of claim 1, wherein said waterborne shape memory polymer forms a semi-spherical particle with other waterborne shape memory polymers when dispersed in water, wherein said hydrophobic switching segment of each of said other waterborne shape memory polymers are surrounded by said chargeable units of each of said other waterborne shape memory polymers.

3. A waterborne shape memory polymer coating and substrate complex comprising the waterborne shape memory polymer of claim 1 and a substrate selected from a group consisting of natural fabrics, synthetic fabrics, and monofilament wires.

4. The waterborne shape memory polymer of claim 1, wherein the switching segment is uncharged.

5. The waterborne shape memory polymer of claim 3, wherein the switching segment is uncharged.

* * * * *